US012698467B2

(12) United States Patent
Goss et al.

(10) Patent No.: US 12,698,467 B2
(45) Date of Patent: Aug. 4, 2026

(54) TISSUE ENGINEERED SCAFFOLDS, INSTRUMENTED BIOREACTORS AND METHODS OF USE THEREOF

(71) Applicant: President and Fellows of Harvard College, Cambridge, MA (US)

(72) Inventors: Josue A. Goss, Rogers, AR (US); Christophe Chantre, Cambridge, MA (US); Luke A. MacQueen, Cambridge, MA (US); Kevin Kit Parker, Cambridge, MA (US)

( * ) Notice: Subject to any disclaimer, the term of this patent is extended or adjusted under 35 U.S.C. 154(b) by 1188 days.

(21) Appl. No.: 16/968,178

(22) PCT Filed: Feb. 5, 2019

(86) PCT No.: PCT/US2019/016572
§ 371 (c)(1),
(2) Date: Aug. 7, 2020

(87) PCT Pub. No.: WO2019/156941
PCT Pub. Date: Aug. 15, 2019

(65) Prior Publication Data
US 2021/0371790 A1 Dec. 2, 2021

Related U.S. Application Data

(60) Provisional application No. 62/627,799, filed on Feb. 8, 2018.

(51) Int. Cl.
*C12M 1/12* (2006.01)
*C12M 1/00* (2006.01)
(Continued)

(52) U.S. Cl.
CPC ............ *C12M 25/14* (2013.01); *C12M 21/08* (2013.01); *C12M 23/20* (2013.01); *C12M 29/00* (2013.01);
(Continued)

(58) Field of Classification Search
CPC ...... C12M 25/14; C12M 21/08; C12M 23/20; C12M 29/00; C12M 41/44
See application file for complete search history.

(56) References Cited

U.S. PATENT DOCUMENTS 1,500,934 A 7/1924 Hooper
1,975,504 A 10/1934 Formhals
(Continued)

FOREIGN PATENT DOCUMENTS

CN 1710160 A 12/2005
CN 101538745 A 9/2009
(Continued)

OTHER PUBLICATIONS

Harfenist , S., et al., Direct Drawing of Suspended Filamentary Micro- and Nanostructures from Liquid Polymers. Nano Letters, 2004;4(10):1931-1937.
(Continued)

*Primary Examiner* — Michael A Marcheschi
*Assistant Examiner* — Jonathan E Lepage
(74) *Attorney, Agent, or Firm* — McCarter & English, LLP; Maria Laccotripe Zacharakis

(57) ABSTRACT

Systems and methods are provided including a housing configured to receive and engage a hollow tissue structure within a fluid chamber of the housing. A first pair of flow channels and a second pair of flow channels of the housing are fluidly coupled to the fluid chamber. The housing fluidly couples the first pair of flow channels and fluidly couples the second pair of flow channels via a second flow path such that a change in a fluid pressure differential between a first fluid in the first flow path and a second fluid in the second flow path deflects at least a portion of the hollow tissue structure causing a change in flow of the first fluid through the first
(Continued)

pair of flow channels or a change in flow of the second fluid through the second pair of flow channels.

19 Claims, 28 Drawing Sheets

(51) Int. Cl.

| | |
|---|---|
| C12M 1/34 | (2006.01) |
| C12M 3/00 | (2006.01) |
| C12N 5/071 | (2010.01) |
| C12N 5/077 | (2010.01) |
| G01N 33/50 | (2006.01) |

(52) U.S. Cl.

CPC ........... *C12M 41/44* (2013.01); *C12N 5/0652* (2013.01); *C12N 5/0697* (2013.01); *G01N 33/5088* (2013.01); *C12N 2503/02* (2013.01)

(56) References Cited

U.S. PATENT DOCUMENTS

| | | | |
|---|---|---|---|
| 2,067,410 | A | 1/1937 | Newnham |
| 2,138,394 | A | 11/1938 | Wuppermann |
| 2,336,743 | A | 12/1943 | Lozano et al. |
| 2,988,469 | A | 6/1961 | Watson |
| 3,038,779 | A | 6/1962 | Georg et al. |
| 3,441,473 | A | 4/1969 | Brundige |
| 4,237,081 | A | 12/1980 | Murphy et al. |
| 4,345,355 | A | 8/1982 | Berchoux et al. |
| 4,374,978 | A | 2/1983 | Fujiwara et al. |
| 4,536,361 | A | 8/1985 | Torobin |
| 4,702,876 | A | 10/1987 | Ebregt et al. |
| 5,066,430 | A | 11/1991 | Matthews |
| 5,246,776 | A | 9/1993 | Meraldi et al. |
| 5,441,754 | A | 8/1995 | Evans, Sr. |
| 5,447,423 | A | 9/1995 | Fuisz et al. |
| 5,494,616 | A | 2/1996 | Voelker et al. |
| 6,113,818 | A | 9/2000 | Pellegrin et al. |
| 6,159,597 | A | 12/2000 | Meerman et al. |
| 6,207,274 | B1 | 3/2001 | Ferenc et al. |
| 6,382,526 | B1 | 5/2002 | Reneker et al. |
| 6,596,048 | B1 | 7/2003 | Tuffal et al. |
| 8,080,197 | B2 | 12/2011 | Meerman et al. |
| 8,192,981 | B2 | 6/2012 | Hoerstrup et al. |
| 8,399,243 | B2 | 3/2013 | Bouten et al. |
| 8,617,237 | B2 | 12/2013 | Hoerstrup et al. |
| 8,636,793 | B2 | 1/2014 | Hoerstrup et al. |
| 9,410,267 | B2 | 8/2016 | Parker et al. |
| 9,669,141 | B2 | 6/2017 | Parker et al. |
| 9,738,046 | B2 | 8/2017 | Parker et al. |
| 10,519,569 | B2 | 12/2019 | Parker et al. |
| 11,174,571 | B2 | 11/2021 | Parker et al. |
| 2002/0148050 | A1 | 10/2002 | Luo et al. |
| 2002/0182241 | A1 | 12/2002 | Borenstein et al. |
| 2003/0147983 | A1 | 8/2003 | Berrigan et al. |
| 2003/0187500 | A1 | 10/2003 | Jansen et al. |
| 2003/0199083 | A1 | 10/2003 | Vilendrer et al. |
| 2004/0034408 | A1 | 2/2004 | Majercak et al. |
| 2004/0037813 | A1 | 2/2004 | Simpson et al. |
| 2004/0093080 | A1 | 5/2004 | Helmus et al. |
| 2004/0234571 | A1 | 11/2004 | Jang |
| 2005/0043209 | A1 | 2/2005 | Schmiedel et al. |
| 2005/0136253 | A1 | 6/2005 | Michael et al. |
| 2005/0143810 | A1 | 6/2005 | Dauner et al. |
| 2005/0163932 | A1 | 7/2005 | Zschieschang et al. |
| 2005/0209687 | A1 | 9/2005 | Sitzmann et al. |
| 2005/0240262 | A1 | 10/2005 | White |
| 2006/0060999 | A1 | 3/2006 | Amagasa et al. |
| 2006/0094096 | A1 | 5/2006 | Wang et al. |
| 2006/0105275 | A1 | 5/2006 | Maloney et al. |
| 2006/0228435 | A1 | 10/2006 | Andrady et al. |
| 2006/0246584 | A1 | 11/2006 | Covelli |
| 2007/0087178 | A1 | 4/2007 | Hendriks et al. |
| 2007/0207186 | A1 | 9/2007 | Scanlon et al. |

| | | | |
|---|---|---|---|
| 2008/0023888 | A1 | 1/2008 | Brang et al. |
| 2008/0038352 | A1 | 2/2008 | Simpson et al. |
| 2008/0131965 | A1 | 6/2008 | Baaijens |
| 2008/0136054 | A1 | 6/2008 | Fabbricante et al. |
| 2008/0145596 | A1 | 6/2008 | Levit et al. |
| 2008/0211121 | A1 | 9/2008 | Lai et al. |
| 2008/0237934 | A1 | 10/2008 | Reneker et al. |
| 2008/0242171 | A1 | 10/2008 | Huang et al. |
| 2008/0281434 | A1 | 11/2008 | Schmidt et al. |
| 2008/0299160 | A1 | 12/2008 | Agboh et al. |
| 2008/0307766 | A1 | 12/2008 | Petras et al. |
| 2009/0209982 | A1 | 8/2009 | Hoerstrup et al. |
| 2009/0232874 | A1 | 9/2009 | Chu et al. |
| 2009/0232920 | A1 | 9/2009 | Lozano et al. |
| 2009/0233361 | A1 | 9/2009 | Farhat et al. |
| 2009/0269429 | A1 | 10/2009 | Lozano et al. |
| 2009/0280207 | A1 | 11/2009 | Lozano et al. |
| 2009/0280325 | A1 | 11/2009 | Lozano et al. |
| 2010/0028999 | A1 | 2/2010 | Nain |
| 2010/0037576 | A1 | 2/2010 | Claasen et al. |
| 2010/0233928 | A1 | 9/2010 | Ferry et al. |
| 2011/0073243 | A1 | 3/2011 | Yu et al. |
| 2011/0263729 | A1 | 10/2011 | Hermanutz et al. |
| 2012/0135448 | A1 | 5/2012 | Parker et al. |
| 2013/0217128 | A1 | 8/2013 | Bouten et al. |
| 2013/0312638 | A1 | 11/2013 | Parker et al. |
| 2013/0344531 | A1 | 12/2013 | Akra et al. |
| 2014/0005772 | A1 | 1/2014 | Edelman et al. |
| 2014/0023703 | A1 | 1/2014 | Fernandez et al. |
| 2014/0090141 | A1 | 4/2014 | Friedrich |
| 2014/0272318 | A1 | 9/2014 | Lawrence et al. |
| 2015/0182679 | A1 | 7/2015 | Parker et al. |
| 2015/0354094 | A1 | 12/2015 | Parker et al. |
| 2016/0220361 | A1 | 8/2016 | Weber et al. |
| 2016/0235527 | A1 | 8/2016 | Sanders et al. |
| 2016/0331528 | A1 | 11/2016 | Parker et al. |
| 2017/0360551 | A1 | 12/2017 | Liu |
| 2019/0343190 | A1 | 11/2019 | Ogunbiyi et al. |
| 2020/0376170 | A1 | 12/2020 | Ahn et al. |
| 2021/0205076 | A1 | 7/2021 | Parker et al. |
| 2021/0371790 | A1 | 12/2021 | Macqueen et al. |
| 2022/0090300 | A1 | 3/2022 | Liu et al. |
| 2022/0136136 | A1 | 5/2022 | Parker et al. |

FOREIGN PATENT DOCUMENTS

| | | | | |
|---|---|---|---|---|
| CN | 101824382 A | | 9/2010 | |
| CN | 101871133 A | | 10/2010 | |
| CN | 203360644 U | | 12/2013 | |
| CN | 103805511 A | | 5/2014 | |
| CN | 105142652 A | * | 12/2015 | .......... A01N 1/0263 |
| CN | 108842195 A | | 11/2018 | |
| DE | 1170578 B | | 5/1964 | |
| EP | 1077072 A2 | | 2/2001 | |
| EP | 1499366 B1 | | 7/2007 | |
| EP | 1858450 A1 | | 11/2007 | |
| EP | 1968660 B1 | | 11/2010 | |
| EP | 2267114 A2 | | 12/2010 | |
| EP | 1663332 B1 | | 1/2011 | |
| EP | 1957632 B1 | | 5/2012 | |
| EP | 2617389 A1 | | 7/2013 | |
| EP | 2117476 B1 | | 1/2014 | |
| EP | 2117477 B1 | | 4/2014 | |
| EP | 1974009 B1 | | 9/2015 | |
| EP | 2997935 A1 | | 3/2016 | |
| EP | 3049025 A1 | | 8/2016 | |
| EP | 3049026 A1 | | 8/2016 | |
| IL | 62097 A | | 7/1985 | |
| JP | 2006-311887 A | | 11/2006 | |
| JP | 2010-031434 A | | 2/2010 | |
| JP | 2013-53398 A | | 3/2013 | |
| KR | 92-8999 B1 | | 10/1992 | |
| KR | 10-2006-0010102 A | | 2/2006 | |
| KR | 20110121924 A | | 11/2011 | |
| KR | 101104336 B1 | | 1/2012 | |
| NL | 1008349 C2 | | 8/1999 | |
| WO | WO-2003/099230 A2 | | 12/2003 | |
| WO | WO-2004/032713 A2 | | 4/2004 | |
| WO | WO-2004060426 A1 | * | 7/2004 | .......... A61L 27/3839 |

(56) References Cited

FOREIGN PATENT DOCUMENTS

| WO | WO-2004/080681 A1 | 9/2004 | | |
|----|-------------------|--------|---|---|
| WO | WO-2005/017226 A1 | 2/2005 | | |
| WO | WO-2010/041944 A1 | 4/2010 | | |
| WO | WO-2010/132636 A1 | 11/2010 | | |
| WO | WO-2012/068402 A2 | 5/2012 | | |
| WO | WO-2013/018021 A1 | 2/2013 | | |
| WO | WO-2014172575 A1 * | 10/2014 | ........... | C12M 21/08 |
| WO | WO-2015/112839 A1 | 7/2015 | | |
| WO | WO-2015/184273 A1 | 12/2015 | | |
| WO | WO-2016/007879 A1 | 1/2016 | | |
| WO | WO-2016/036532 A1 | 3/2016 | | |
| WO | WO-2017/083381 A1 | 5/2017 | | |
| WO | WO-2018/064393 A1 | 4/2018 | | |
| WO | WO-2019/108712 A1 | 6/2019 | | |
| WO | WO-2019/156941 A1 | 8/2019 | | |
| WO | WO-2020/150207 A1 | 7/2020 | | |
| WO | WO-2021/087371 A1 | 5/2021 | | |

OTHER PUBLICATIONS

Li, D. and Xia, Y. Electrospinning of nanofibers: Reinventing the wheel? Advanced Materials 2004;16(14):1151-1170.

Feinberg, A.W., et al. Muscular Thin Films for Building Actuators and Powering Devices. Science 2007; 317(5843):1366-1370.

Arumuganathar, S. and Jayasinghe, S.N. Living Scaffolds (Specialized and Unspecialized) for Regenerative and Therapeutic Medicine. Biomacromolecules 2008; 9(3):759-766.

Weitz R.T., et al. Polymer Nanofibers via Nozzle-Free Centrifugal Spinning. Nano Letters 2008;8(4):1187-1191.

Xie, J., et al. Putting Electrospun Nanofibers to Work for Biomedical Research. Macromolecular Rapid Communications 2008;29(22): 1775-1792.

Madurantakam, P.A., et al. Science of nanofibrous scaffold fabrication: strategies for next generation tissue-engineering scaffolds. Nanomedicine 2009;4(2):193-206.

Madurantakam, P.A., et al. Multiple factor interactions in biomimetic mineralization of electrospun scaffolds. Biomaterials 2009; 30(29):5456-5464.

Nisbet D.R., et al. Review paper: a review of the cellular response on electrospun nanofibers for tissue engineering. J Biomater Appl. Jul. 2009;24(1):7-29.

Pabba, S., et al. Biopolymerization-driven self-assembly of nanofiber air-bridges. Soft Matter 2009;5(7):1378-1385.

Alford P.W., et al. Biohybrid thin films for measuring contractility in engineered cardiovascular muscle. Biomaterials. 2010;31(13):3613-3621.

International Search Report and Written Opinion in PCT/US11/61241, mailed Apr. 11, 2012.

International Search Report and Written Opinion in PCT/US10/34662, mailed Jul. 9, 2010.

European Search Report in 12867106.2, mailed Sep. 25, 2015.

International Search Report and Written Opinion in PCT/US2012/065646, mailed Aug. 27, 2013.

International Search Report and Written Opinion in PCT/US14/16197, mailed Jul. 30, 2014.

Kolk, "Mathematical Models for a Rotor Spinning Process Interim report", Jan. 2005.

Badrossamay, M.R. et al. "Nanofiber assembly by rotary jet-spinning." Nano Letters, May 2010;10(6):2257-2261.

Van Lieshout et al., "Electrospinning versus knitting: two scaffolds for tissue engineering of the aortic valve", J. Biomater. Sci. Polymer Edn, vol. 17, No. 1-2, pp. 77-89 (2006).

Bansal et al. Water-Based Polymeric Nanostructures for Agricultural Applications. dem Fachbereich Chemie der Philipps-Universitat Marburg. 2010.

International Search Report and Written Opinion in PCT/US2017/054125, mailed on Jan. 9, 2018.

Bauer, C. et al. A Novel Cross-Linked Hyaluronic Acid Porous Scaffold for Cartilage Repair: An In Vitro Study With Osteoarthritic Chondrocytes. Cartilage. 2016, vol. 7, No. 3; pp. 265-273.

Lam, J, et al. Design of Cell-Matrix Interactions in Hyaluronic Acid Hydrogel Scaffolds. Acta Biomater. Apr. 1, 2015, vol. 10, No. 4; pp. 1571-1580.

Baker, S, et al. The Mechanical Properties of Dry, Electrospun Fibrinogen Fibers. Mar. 1, 2012, vol. 32, No. 2; pp. 215-221.

Bhowmick, S, et al. Fabrication and Evaluation of Polymeric Hybrid Scaffolds for Skin Tissue Engineering. Submitted in Fulfilment of the Requirements of the Degree of Doctor of Philosophy to the Indian Institute of Technology Delhi. Centre for Biomedical Engineering: Indian Institute of Technology. Apr. 2017; p. iii, Abstract, Second Paragraph; p. iii, Abstract, Fourth Paragraph; p. xv; p. xviii.

Gallos, A, et al. Lignocellulosic Fibers: A Critical Review of the Extrusion Process for Enhancement of the Properties of Natural Fiber Composites. RSC Adv. Jun. 30, 2017, vol. 7, pp. 34638-34654; p. 34641, Left Column, Second Paragraph; p. 34638, Abstract; p. 34642, Right Column, Third Paragraph to p. 34643, Left Column, First Paragraph; p. 34643, Table 1.

Da, LC, et al. Progress in Development of Bioderived Materials for Dermal Wound Healing. Regnerative Biomaterials. Aug. 24, 2017, pp. 325-334. DOI: 10.1093/rb/rbx025; p. 325, Abstract, Right Column, Second Paragraph; p. 327, Right Column, First Paragraph; p. 330, Left Column, Second Paragraph.

Kanis, LA, et al. Cellulose Acetate Butyrate/Poly(caprolactonetriol) Blends: Miscibility, Mechanical Properties, and In Vivo Inflammatory Response. Journal of Biomaterial Applications. Jul. 11, 2014, vol. 0, No. O; pp. 1-8.

Ahmad, Z, et al. Effect of 1-ethyl-3-(3-dimethylaminopropyl) Carbodiimide and N-hydroxysuccinimide Concentrations on the Mechanical and Biological Characteristics of Cross-Linked Collagen Fibres for Tendon Repair. Regenerative Biomaterials. May 16, 2015, pp. 77-85.

International Search Report and Written Opinion in PCT/US2018/059722, mailed Jan. 30, 2019.

Da et al., "Progress in development of bioderived materials for dermal wound healing", Regen Biomater. Oct. 2017; 4(5): 325-334.

Bansal et al. Water-stable all-biodegradable microparticies in nanofibers by electrospinning of aqueous dispersions for biotechnical plant protection. Biomacromolecules.Feb. 13, 2012;13(2):439-44.

International Search Report and Written Opinion for Application No. PCT/US2016/061129, dated Apr. 14, 2017, 7 pages.

Ghayempour et al., Micro/nanoencapsulation of essential oils and fragrances: Focus on perfumed, antimicrobial, mosquito-repellent and medical textiles. J Microencapsul. Sep. 2016;33(6):497-510.

Sarier et al., Organic phase change materials and their textile applications: An overview. Thermochimica Acta. Jul. 20, 2012;540:7-60.

Teeka et al., Preparation of Poly (methyl methacrylate) microcapsule with encapsulated Jasmine oil. Energy Procedia. 2014;56:181-186.

International Search Report and Written Opinion for Application No. PCT/US2019/016572, dated Apr. 15, 2019, 15 pages.

MacQueen et al., A tissue-engineered scale model of the heart ventricle. Nat Biomed Eng. Dec. 2018;2(12):930-941.

Supplementary European Search Report for Application No. 19750902.9, dated Oct. 8, 2021, 7 pages.

International Search Report and Written Opinion for Application No. PCT/US2020/013466, dated Apr. 6, 2020, 10 pages.

International Search Report and Written Opinion for Application No. PCT/US2020/058379, dated Mar. 10, 2021, 10 pages.

U.S. Appl. No. 13/320,031, filed Jan. 30, 2012, US 2012-0135448, Granted.

U.S. Appl. No. 15/203,924, filed Jul. 7, 2016, Abandoned.

U.S. Appl. No. 13/988,088, filed Aug. 5, 2013, US 2013-0312638, Abandoned.

U.S. Appl. No. 14/359,005, filed May 16, 2014, US 2014-0322515, Granted.

U.S. Appl. No. 14/763,620, filed Jul. 27, 2015, US 2015-0354094, Granted.

U.S. Appl. No. 16/679,578, filed Nov. 11, 2019, US 2020-0318258, Granted.

U.S. Appl. No. 17/501,005, filed Oct. 14, 2021, US 2022-0136136, Published.

(56) References Cited

OTHER PUBLICATIONS

U.S. Appl. No. 15/112,528, filed Jul. 19, 2016, US 2016-0331528, Abandoned.
U.S. Appl. No. 17/102,495, filed Jul. 8, 2021, US 2021-0205076, Abandoned.
PCT/US2016/061129, Nov. 9, 2016, WO 2017/083381, Published.
PCT/US2017/054125, Sep. 28, 2017, WO 2018/064393, Published.
U.S. Appl. No. 16/762,384, filed May 7, 2020, US 2020-0376170, Abandoned.
PCT/US2018/059722, Nov. 8, 2018, WO 2019/094526, Published.
PCT/US2019/016572, Feb. 5, 2019, WO 2019/156941, Published.
U.S. Appl. No. 17/421,047, filed Jul. 7, 2021, US 2022-0090300, Published.
PCT/US2020/013466, Jan. 14, 2020, WO 2020/150207, Published.
U.S. Appl. No. 17/771,530, filed Apr. 25, 2022, US 2022-0380943, Published.
PCT/US2020/058379, Oct. 30, 2020, WO 2021/087371, Published.

* cited by examiner

Flow Loop Schematic

Flow loop 1

Intra-ventricular flow loop: → To connect with other organs or systems

Flow loop 2

Extra-ventricular assist flow loop: → Applied flow drives ventricle deformation and flow in loop 1

Back
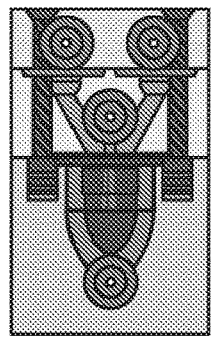
Side
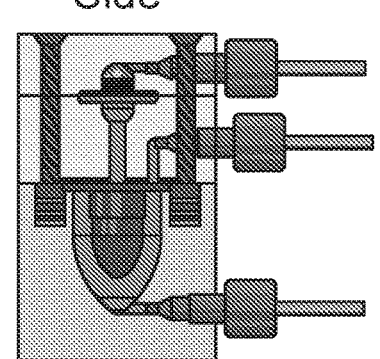
44
42
38
32,34
108
16
40
104
102
28
35
32,34
36
14
34
32
30
100
106
18
24
22
26
12
23
20
FIG. 1D           FIG. 1E
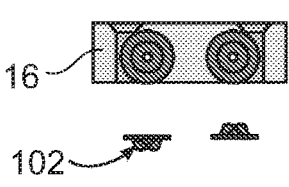
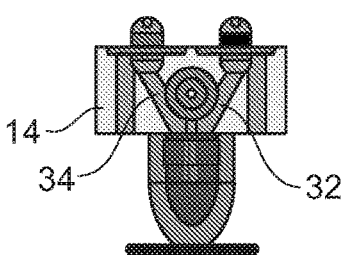
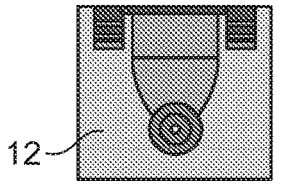
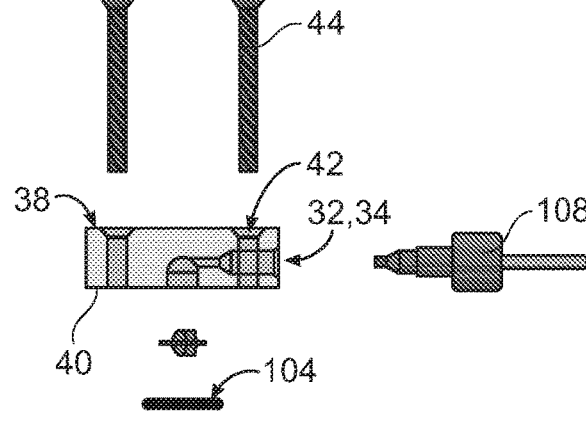
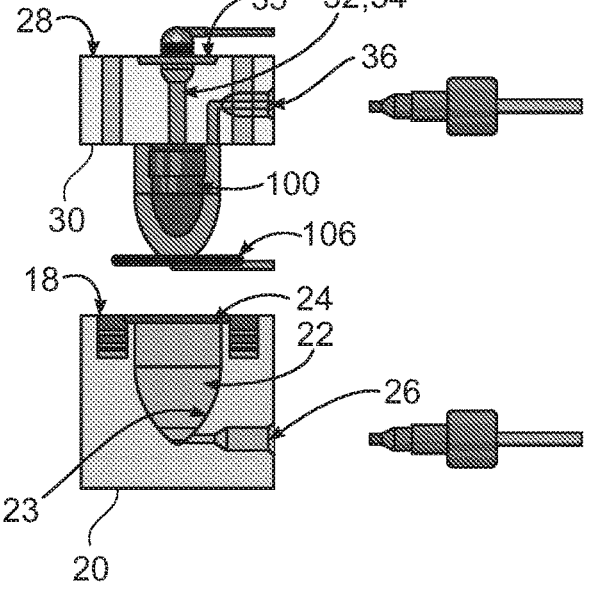

200

208

204

100

22

202

206

208

Two-component HBR base for window insertion

200

Two windowed HBRs

200 a   Heart bioreactor (HBR) for modular assembly of ventricles and valves

C  Ultrasound with or without HBR-assisted ventricle contraction

A Cast molding silicone valves and ventricles top
bottom 2 mm top
bottom 1 mm

Top

Four HBRs

Front

Side

B HBR Photos d   3D calcium propagation on tissue-engineered ventricle surfaces c   Scaffold structure (μCT)

A   Pull spinning (PS) a nanofibrous ventricle scaffold: Schematic overview (i) Fiber collection (ii) Schematic of fiber formation and collection

B Pull spinning (PS) platform CAD Drawings

Stage-mounted motor for bristle rotation

Rotating bristle

Fibers (blue)

Needle

Stage-mounted motor for collector rotation rotating collector

Airflow

Solution fed via syringe to needle

Left ventricle collector CAD drawings

SECTION A-A

9

18

9

4.500

Ø9

Ø4.200 ⤓ 12.400
M5X0.8 - 6H ⤓ 10

1 Left ventricle collector

Sheet collector

Coverslip collector

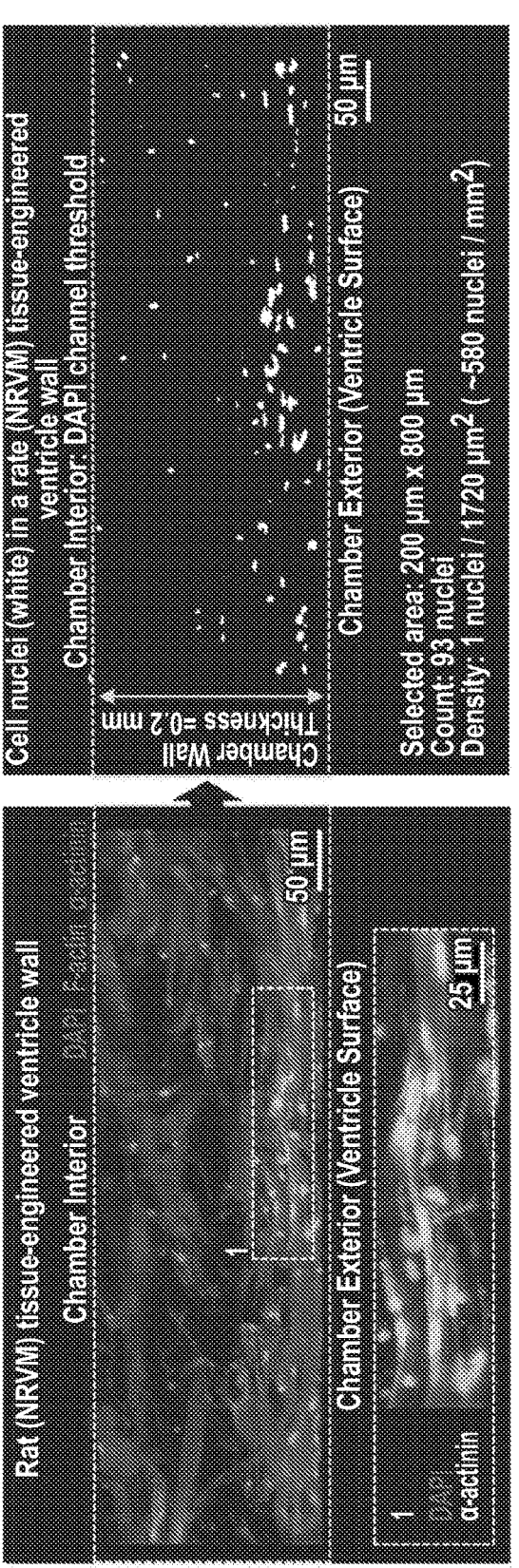

A Comparison of rat and tissue-engineered (TE)-rat left ventricle (LV) wall cross-section immunostaining

Rat LV wall
- vascularized
- ~2 mm thick
- ~100 cell layers

TE LV wall
- avascular
- ~0.2 mm thick
- ~5-10 cell layers
- exterior cell seeding Rat Heart TE Ventricle epicardium endocardium 5 mm 100 μm 10 μm 3 mm

FIG. 11A

B Transmural cell distribution in a tissue-engineered rat (NRVM) ventricle

Rat (NRVM) tissue-engineered ventricle wall

Chamber Interior

Chamber Exterior (Ventricle Surface)

50 μm

25 μm

α-actinin

Cell nuclei (white) in a rate (NRVM) tissue-engineered ventricle wall

Chamber Interior: DAPI channel threshold

Chamber Wall Thickness = ~0.2 mm

Chamber Exterior (Ventricle Surface)

50 μm

Selected area: 200 μm x 800 μm
Count: 93 nuclei
Density: 1 nuclei / 1720 μm² (~580 nuclei / mm²)

FIG. 11B

C  Cell alignment quantified by an Orientational Order Parameter (OOP)

A Tissue-engineered ventricle catheterization for pressure-volume (PV) measurement Ventricle catheterization on a temperature-controlled stage-mounted plate Ventricle sutured to tubing Ventricle and catheter prior to suturing

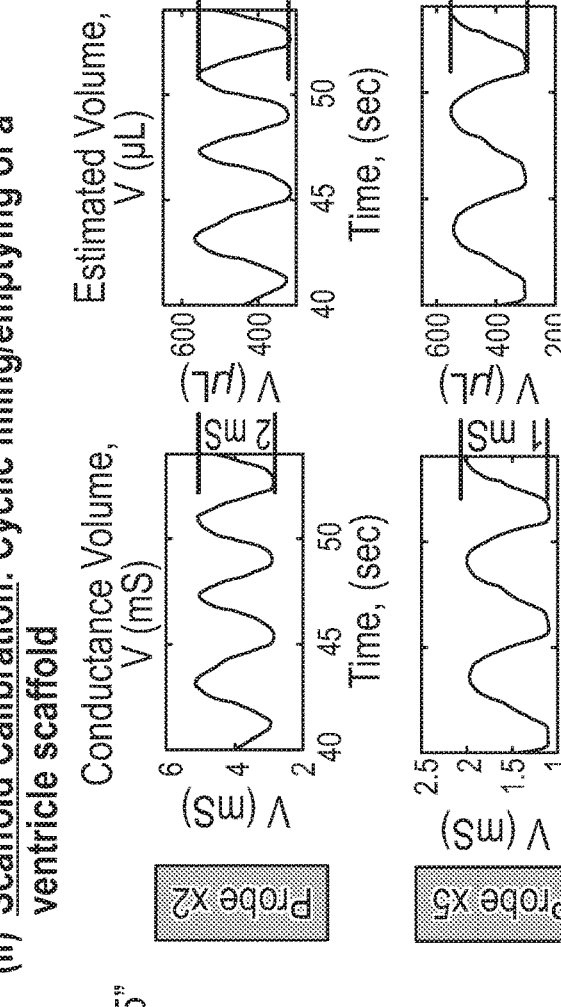
FIG. 12B

TISSUE ENGINEERED SCAFFOLDS, INSTRUMENTED BIOREACTORS AND METHODS OF USE THEREOF

CROSS-REFERENCE TO RELATED APPLICATIONS

This application is a 35 U.S.C. § 371 national stage filing of International Application No. PCT/US2019/016572, filed on Feb. 5, 2019, which in turn claims priority to and benefit of U.S. Provisional Application No. 62/627,799, entitled "Tissue Engineered Scaffolds, Instrumented Bioreactors and Methods of Use Thereof", filed on Feb. 8, 2018. The entire contents of each of the foregoing applications are incorporated herein by reference.

GOVERNMENT SUPPORT

This invention was made with Government support under contract DE-AC52-06NA25396 awarded by the Defense Threat Reduction Agency (DTRA), and under grant number HL141798 awarded by the National Institute of Health (NIH). The government has certain rights in the invention.

TECHNICAL FIELD

Embodiments of the disclosure relate to a housing configured and dimensioned to assist with ventricular flow (e.g., testing, preparation/fabrication).

BACKGROUND OF THE INVENTION

Laboratory models of the heart are used to gain a mechanistic understanding of heart function in health and disease, and to test the safety and efficacy of potential therapeutics. The heart is studied at multiple scales in vitro, from cellular assays to excised or engineered tissues and "organ-on-chip" microphysiological systems (Benam, K. H. et al. *Annu Rev Pathol* 10, 195-262, 2015) that recapitulate integrated aspects of specific pathological conditions. Functional read-outs obtained using engineered heart tissues include contractile forces and electrophysiological measurements (Tzatzalos, E. et al., *Adv Drug Del Rev* 96, 234-244, 2016), but direct comparison with natural ventricle pressure and volume dynamics requires three-dimensional (3D) contractile cardiac chambers. To obtain these measurements, animal models and isolated heart preparations are evaluated using pre-clinical and clinical measurement modalities such as catheterization (Pacher, P., et al. *Nat Protoc* 3, 1422-1434, doi:10.1038/nprot.2008.138 (2008)), echocardiography (Ram, R. et al., *American journal of physiology. Heart and circulatory physiology* 301, H1765-1780, 2011), and magnetic resonance imaging (Bakermans, A. J. et al. *Progress in Nuclear Magnetic resonance spectroscopy* 88-89, 1-47, 2015). Data obtained using these methods allow direct comparison to patient data, but differences in genetics, physiology and disease etiology limit the utility of animal models for developing therapeutic interventions (Chandrasekera, P. C. & Pippin, J. *J. Am J Transl Res* 7, 1636-1647, 2015). These and other limitations associated with animal models, for example high maintenance costs and low experimental throughput, motivate the development of alternative in vitro cardiology platforms based on human cells.

Human induced pluripotent stem cell-derived cardiomyocytes (hiPSC-CM) have emerged as a promising tool for in vitro cardiology, with the potential to eliminate interspecies and interpersonal variations through patient-specific derivation (Karakikes, I., et al., *Circ Res* 117, 80-88, 2015). These cells are assembled into functional engineered heart tissues (Tzatzalos, E. et al., *Adv Drug Deliv Rev* 96, 234-244, 2016; Feric, N. T. & Radisic, M. *Adv Drug Deliv Rev* 96, 110-134, 2016; and Eder, A. et al., *Adv Drug Deliver Rev* 96, 214-224, 2016), including muscular thin films (Wang, G. et al. *Nat Med* 20, 616-623, 2014; and Lind, J. U. et al. *Nat Mater,* 2016) or 3D muscle strips (Boudou, T. et al. *Tissue engineering. Part A* 18, 910-919, 2012; Nunes, S. S. et al. *Nat Methods* 10, 2013; Thavandiran, N. et al. *PNAS, USA* 110, E4698-4707, 2013; Mannhardt, I. et al. *Stem Cell Reports* 7, 29-42, 2016; Huebsch, N. et al. *Sci Rep* 6, 24726, 2016; Mathur, A. et al. *Sci Rep* 5, 8883, 2015; Turnbull, I. C. et al. *FASEB J* 28, 644-654, 2014; and Sidorov, V. Y. et al. *Acta Biomater* 48, 68-78, 2017), to model contractile pathophysiologies (Wang, G. et al. *Nat Med* 20, 616-623, 2014), promote hiPSC-CM maturation (Feric, N. T. & Radisic, M. *Adv Drug Deliv Rev* 96, 110-134, 2016; Nunes, S. S. et al. *Nat Methods* 10, 2013; Thavandiran, N. et al. *PNAS, USA* 110, E4698-4707, 2013; and Godier-Furnemont, A. F. G. et al. *Biomaterials* 60, 82-91, 2015), and produce drug responses that are increasingly comparable to human patients (Mannhardt, I. et al. *Stem Cell Reports* 7, 29-42, 2016; Mathur, A. et al. *Sci Rep* 5, 8883, 2016; and Tiburcy, M. et al. *Circulation,* 116.024145, 2011). There are, however, no in vitro models based on hiPSC-CM that accurately reproduce the architecture and functional output of the heart chambers (Feric, N. T. & Radisic, M. *Adv Drug Deliv Rev* 96, 110-134, 2016; Eder, A., Vollert, I., Hansen, A. & Eschenhagen, T. *Adv Drug Deliver Rev* 96, 214-224, 2016; and Mathur, A., Ma, Z., Loskill, P., Jeeawoody, S. & Healy, K. E. *Adv Drug Deliv Rev* 96, 203-213, 2016). This is a significant limitation because tissue performance cannot be directly compared to animal or human heart performance, which are evaluated by measuring changes in chamber pressure and volume (Pacher, P., et al. *Nat Protoc* 3, 1422-1434, 2008; and Burkhoff, D., Mirsky, I. & Suga, H. *American journal of physiology. Heart and circulatory physiology* 289, H501-512, 2005). Engineered cardiac organoid chambers including neonatal rat cardiomyocytes embedded in an isotropic hydrogel showed significant promise for obtaining intra-ventricular pressure measurements (Lee, E. J., Kim do, E., Azeloglu, E. U. & Costa, K. D. *Tissue engineering. Part A* 14, 215-225, 2008), but the lack of a scaffold to guide cell assembly hampered the formation of organized tissues that recapitulate the laminar architecture (Costa, K. D. et al., *The American journal of physiology* 276, H595-607, 1999; and Arts, T. et al., *Heart and circulatory physiology* 280, H2222-2229, 2001) of the native myocardium.

Accordingly, there is a need in the art for improved pumps and valves that are durable and can mimic the function of the human heart and do not have the side-effects associated with current devices.

SUMMARY OF THE INVENTION

Some embodiments of the present invention include an assembly of a housing (e.g., heart bioreactor) for assisting with the production of ventricular flow. In some embodiments, the disclosed housing may be used for ventricular testing/fabrication, including but not limited to, drug testing, device testing (e.g., LVAD, pacemakers, defibrillator), conditioning stem cells for implantation, growing engineered organs for transplant, and any combination thereof. The parameters of the disclosed housing may be scaled. The operating conditions (e.g., pressure, flow rate) of the disclosed ventricular may be varied. The disclosed housing may be used as an extracorporeal device. The disclosed housing may be applicable to a variety of organs, including but not limited to, heart, uterus, bladder, stomach.

An exemplary embodiment of the present disclosure includes a housing defining a fluid chamber, a first pair of flow channels fluidly coupled to the fluid chamber, and a second pair of flow channels fluidly coupled to the fluid chamber. The housing is configured to receive and engage a hollow tissue structure within the fluid chamber to fluidly couple the first pair of flow channels via a first flow path through an interior of the hollow tissue structure and to fluidly couple the second pair of flow channels via a second flow path. The second flow path extends between an exterior of the hollow tissue structure and a surface of the fluid chamber at least partially surrounding the hollow tissue structure. The housing is configured such that a change in a fluid pressure differential between a first fluid in the first flow path and a second fluid in the second flow path deflects at least a portion of the hollow tissue structure causing a change in flow of the first fluid through the first pair of flow channels or a change in flow of the second fluid through the second pair of flow channels.

In some embodiments, the housing assembly can be used or include a hollow tissue structure including an anisotropic cardiomyocyte assembly on a fibrous scaffold. In some embodiments, the hollow tissue structure includes a 3D tissue-engineered ventricle scaffold formed with a polymeric fiber, e.g., nanofiber, production platform that mimics at least some aspects of human myocardial tissue architecture. Polymeric fibers, e.g., nanofibers, provide biochemical and nano-topographical structural cues with sufficient fidelity to guide cell adhesion, orientation, shape, and assembly. In some embodiments the ventricle-shaped polymeric fiber, e.g., nanofibrous, scaffolds promote cardiomyocyte assembly into functional 3D tissue-engineered ventricle chambers.

In another embodiment, a system may include a housing which may define a fluid chamber, a first pair of flow channels fluidly coupled to the fluid chamber, and a second pair of flow channels fluidly coupled to the fluid chamber. The housing may be configured to receive and engage a hollow tissue structure within the fluid chamber to fluidly couple the first pair of flow channels via a first flow path through an interior of the hollow tissue structure and to fluidly couple the second pair of flow channels via a second flow path extending between an exterior of the hollow tissue structure. A surface of the fluid chamber may at least partially surround the hollow tissue structure such that a change in a fluid pressure differential between a first fluid in the first flow path and a second fluid in the second flow path deflects at least a portion of the hollow tissue structure causing a change in flow of the first fluid through the first pair of flow channels or a change in flow of the second fluid through the second pair of flow channels. The disclosed hollow tissue structure may be disposed within the fluid chamber and may fluidly couple the first pair of flow channels together. The disclosed housing and hollow tissue structure may form a bioreactor.

The disclosed system may further include a pressurizer fluidly coupled to the second pair of flow channels and configured to pressurize the second fluid in the second flow path. The disclosed system may further include at least one valve associated with at least one of the first pair of flow channels and the second pair of flow channels for controlling fluid flow through at least one of the first flow path and the second flow path.

The disclosed system may further include a first fluid source fluidly coupled to the first pair of flow channels for supplying the first fluid and a second fluid source fluidly coupled to the second pair of flow channels for supplying the second fluid. In some embodiments, the first fluid may be different from the second fluid.

The disclosed system may further include a sensor at least partly disposed in the first flow path or fluidly coupled with the first flow path. The sensor may be configured to measure at least one of a fluid pressure in the first flow path and a volume of the hollow tissue structure. The sensor may be in at least partial contact with the hollow tissue structure.

The disclosed housing may further include a window that enables imaging of at least a portion of the fluid chamber. The disclosed window may be fabricated from silicone. The disclosed window may be fabricated from a material that is transparent (e.g., transparent to ultrasound). The housing may include at least two coupled housing portions.

In another embodiment, the housing may include a first portion forming at least a portion of the fluid chamber and at least a portion of at least one of the second pair of flow channels; and a second portion forming at least a portion of the fluid chamber, and at least a portion of each of the first pair of flow channels. The disclosed second portion may also form at least a portion of at least one of the second pair of flow channels. The housing may also include a third portion forming at least a portion of each of the first pair of flow channels.

In some embodiments, the disclosed hollow tissue structure may include a population of cells. The disclosed population of cells may form an anisotropic hollow tissue structure. The disclosed hollow tissue structure including the population of cells may be a natural hollow tissue structure (e.g., a ventricle, a heart, a stomach, an intestine, a uterus, or a bladder). In some embodiments, the disclosed natural hollow tissue structure may be a diseased tissue structure (e.g., an arrhythmic heart). The disclosed hollow tissue structure including the population of cells may be an engineered tissue structure (e.g., a ventricle, a heart, a stomach, an intestine, a uterus, or a bladder). In some embodiments, the disclosed engineered tissue structure may be a diseased tissue structure (e.g., an arrhythmic ventricle).

The disclosed population of cells may be selected from the group including normal cells, abnormal cells, normal cells derived from embryonic stem cells or induced pluripotent stem cells, and diseased cells derived from embryonic stem cells or induced pluripotent stem cells, and combinations thereof. The disclosed population of cells may further include at least one of vascular smooth muscle cells, cardiac myocytes, skeletal muscle cells, uterine smooth muscle cells, intestinal smooth muscle cells, myofibroblasts, airway smooth muscle cells, osteoblasts, myoblasts, neuroblasts, fibroblasts, glioblasts, germ cells, hepatocytes, chondrocytes, keratinocytes, connective tissue cells, glial cells, epithelial cells, endothelial cells, vascular endothelial cells, hormone-secreting cells, neural cells, and cells that will differentiate into muscle cells.

In another embodiment, the disclosed hollow tissue structure may be at least partially coated with a sealant. The disclosed sealant may further include at least one biopolymer. The at least one biopolymer may be selected from the group including a glycosaminoglycans, a gelatin or an alginate, and combinations thereof.

The disclosed hollow tissue structure may be fabricated from by forming micron, submicron or nanometer dimension polymeric fibers, the polymeric fibers configured in a shape of the hollow tissue structure; and seeding cells onto the polymeric fibers. The seeding the cells onto the polymeric fibers may occur outside the fluid chamber.

In a non-limiting example, a method of forming the disclosed system may include placing the hollow tissue structure in the fluid chamber of the housing, the housing defining a first pair of flow channels fluidly coupled to the fluid chamber and a second pair of flow channels fluidly coupled to the fluid chamber. Then, fluidly coupling the first pair of flow channels via a first flow path through an interior of the hollow tissue structure. Then, fluidly coupling the second pair of flow channels via a second flow path extending between an exterior of the hollow tissue structure and a surface of the fluid chamber at least partially surrounding the hollow tissue structure such that a change in a fluid pressure differential between a first fluid in the first flow path and a second fluid in the second flow path deflects at least a portion of the hollow tissue structure causing a change in flow of the first fluid through the first pair of flow channels or a change in flow of the second fluid through the second pair of flow channels. The system may adjust the pressure of the second fluid in the second flow path to induce flow of or change a flow of the first fluid through the first flow path. In some embodiments, the formed system may be a bioreactor.

The hollow tissue structure may be formed by forming micron, submicron or polymeric fibers, e.g., nanometer dimension polymeric fibers, the polymeric fibers configured in a shape of the hollow tissue structure; and seeding cells onto the polymeric fibers. The cells may include at least one of vascular smooth muscle cells, cardiac myocytes, skeletal muscle cells, uterine smooth muscle cells, intestinal smooth muscle cells, myofibroblasts, airway smooth muscle cells, osteoblasts, myoblasts, neuroblasts, fibroblasts, glioblasts, germ cells, hepatocytes, chondrocytes, keratinocytes, connective tissue cells, glial cells, epithelial cells, endothelial cells, vascular endothelial cells, hormone-secreting cells, neural cells, and cells that will differentiate into muscle cells.

The disclosed method may further include flowing the first fluid through the first flow path and flowing the second fluid through the second flow path. In some embodiments, the first fluid may be different from the second fluid.

The disclosed method may further include coating the hollow tissue structure with a sealant. The sealant may include at least one biopolymer. The at least one biopolymer may be selected from the group including a glycosaminoglycans, a gelatin or an alginate, and combinations thereof.

The disclosed method may further include measuring at least one of a fluid pressure in the first flow path and a volume of the hollow tissue structure.

In another non-limiting example, a method for identifying a compound that modulates a hollow tissue function may include providing the system as disclosed throughout the present disclosure. Then, contacting the hollow tissue structure with a test compound. Then, determining the effect of the test compound on a hollow tissue function in the presence and absence of the test compound, wherein a modulation of the hollow tissue function in the presence of the test compound as compared to the hollow tissue function in the absence of the test compound indicates that the test compound modulates a hollow tissue function, thereby identifying a compound that modulates a hollow tissue function.

In some embodiments, the tissue function may be a biomechanical activity. The biomechanical activity may be one or more of contractility, cell stress, cell swelling, and rigidity. The biomechanical activity may also be one or more of stem cell activation, stem cell maturation, tissue morphogenesis, and tissue remodeling. In other embodiments, the tissue function may be an electrophysiological activity. The electrophysiological activity may be a voltage parameter selected from the group including action potential, action potential duration (APD), conduction velocity (CV), refractory period, wavelength, restitution, bradycardia, tachycardia, reentrant arrhythmia, and/or a calcium flux parameter, e.g., intracellular calcium transient, transient amplitude, rise time (contraction), decay time (relaxation), total area under the transient (force), restitution, focal and spontaneous calcium release.

In yet another non-limiting example, a method for identifying a compound useful for treating or preventing a hollow tissue disease may include providing the system as disclosed throughout this disclosure. Then, contacting the hollow tissue structure with a test compound. Then, determining the effect of the test compound on a hollow tissue function in the presence and absence of the test compound, wherein a modulation of the hollow tissue function in the presence of the test compound as compared to the hollow tissue function in the absence of the test compound indicates that the test compound modulates a hollow tissue function, thereby identifying a compound useful for treating or preventing a hollow tissue disease.

In some embodiments, the tissue function may be a biomechanical activity. The biomechanical activity may be one or more of contractility, cell stress, cell swelling, and rigidity. The biomechanical activity may also be one or more of stem cell activation, stem cell maturation, tissue morphogenesis, and tissue remodeling. In other embodiments, the tissue function may be an electrophysiological activity. The electrophysiological activity may be a voltage parameter selected from the group including action potential, action potential duration (APD), conduction velocity (CV), refractory period, wavelength, restitution, bradycardia, tachycardia, reentrant arrhythmia, and/or a calcium flux parameter, e.g., intracellular calcium transient, transient amplitude, rise time (contraction), decay time (relaxation), total area under the transient (force), restitution, focal and spontaneous calcium release.

The embodiments disclosed herein meet these and other needs by providing a system and method for ventricular testing/fabrication.

Other features and advantages of the invention will be apparent from the following detailed description and claims.

BRIEF DESCRIPTION OF THE DRAWINGS

FIG. 1D includes a back view and a back exploded view of the system of FIG. 1C.

FIG. 1E depicts a side view and a side exploded view of the system of FIG. 1C.

FIG. 4A depicts a perspective exploded view, an assembled perspective view and a front view of a system that can be used as an HBR in accordance with some embodiments. FIG. 4A also includes images of a ventricle scaffold and a ventricle scaffold in culture medium. The ventricle wall separates intra- and extra-ventricular flow loops in the assembled HBR. Ventricle scaffolds are sutured over a support ring where input and output channels of the intra-ventricular flow loop converge. Pressure supplied by an external source to the extra-ventricular flow loop drives assisted ventricle contraction and flow through the intra-ventricular flow loop.

FIG. 4B includes graphs illustrating how ventricle catheterization in the HBR enabled pressure and volume measurements during assisted ventricle contraction with or without cast-molded silicone tricuspid valves. FIG. 4B also includes images of ventricle catheterization in the HBR.

FIG. 4C includes echocardiographic measurements of a tissue-engineered neonatal rat ventricular myocyte (NRVM) ventricle contracting unassisted (left) and a cell-free ventricle scaffold contracting by HBR assist (right). In both cases, cross-sections (brightness mode) and time-dependent traces of the ventricle wall (motion, M-mode) are shown.

FIG. 6A includes a schematic overview of the design-build-test project phases, from left to right: Human left ventricle ellipsoidal shape and fibrous extra-cellular matrix (ECM) inspired the use of circumferentially oriented nano-fibers in scale-model ellipsoidal ventricle scaffolds in accordance with some embodiments. The scaffolds were seeded with cardiomyocytes to produce tissue-engineered ventricles and their contractility was evaluated by pressure-volume catheterization.

FIG. 6B illustrates scaffold production by pull spinning (PS): A high-speed rotating bristle dips into a fixed, continuous polymer source that is fed via syringe pump through a small orifice (in this case a needle). The bristle pulls the polymer column into a polymer jet that is ejected towards a rotating collector. Solvent evaporation occurs as the polymer jet travels towards the collection mandrel, where the resulting nanofibers are collected. The resulting ventricle scaffolds are removed from the collector by tweezers in a hydration bath.

FIG. 6C includes micro-computed tomography ($\mu$CT) images of an example ventricle scaffold produced in accordance with some embodiments described herein.

FIG. 6D includes calcium propagation imaging of the functionality of example ventricles produced in accordance with some embodiments described herein. Spontaneous activity produced propagating waves but they did not always originate at the apex (left). Field stimulation, resulting from electrical pacing where electrodes were placed far from the ventricle surface, produced uniform calcium activation (middle). Apical point stimulation (indicated by arrows) produced calcium waves that propagated from apex to base at a rate of 9.33 cm/sec for NRVM ventricles and 5.2 cm/sec for pluripotent stem cell-derived cardiomyocytes (hiPSC-CM) ventricles (right).

FIG. 7A illustrates fiber collection on a left-ventricle-shaped ellipsoidal collection mandrel (i) and schematic overview of the pull-spinning process (ii): A rotating bristle dips and pulls a polymer solution that is extruded from a needle (1, 2); jet elongation (3) and solvent evaporation (4) produce fibers (5) that are collected on a rotating ellipsoidal collection mandrel (6) in accordance with some embodiments.

FIG. 7B illustrates a pull spinning platform showing ventricle, sheet, and coverslip fiber collectors in accordance with some embodiments.

FIG. 8A illustrates a schematic of ventricle surface or cross-section immunostains shown in FIG. 8B (surface) and FIG. 8C (cross-section). In all cases, cells were introduced via the exterior surface. Immunostaining confirmed that cardiomyocytes infiltrated the scaffold and were aligned roughly circumferentially, coincident with the scaffold's nanofiber ultrastructure.

FIG. 9A illustrates an overview of the ventricle catheterization procedure. Catheters were fed through tubing on which the ventricle base was sutured. Ventricles were submerged within a 3.5 cm petri dish bath, which was mounted on a temperature-controlled heating stage. Catheter readouts fed to signal amplification instruments provided real-time measurements of intra-ventricular pressure and volume.

FIG. 9B includes graphs PV measurements obtained by catheterization of example neonatal rat ventricular myocyte (NRVM)—or human induced pluripotent stem cell-derived cardiomyocyte (hiPSC-CM)-based tissue-engineered ventricles. Exposure to isoproterenol (Iso) reduced stroke work of both rat and human ventricles. Here, pressure and volume were normalized by polynomial fit to remove measurement drift occurring over the course of multiple doses.

FIG. 9C illustrates Iso-dependent beat rates for example rat and human tissue-engineered ventricles. Time-domain recordings of chamber volume were Fourier-transformed to obtain beat rates. The spontaneous beat rate of NRVM ventricles (~130±15 bpm) was higher than hiPSC-CM ventricles (~85±15 bpm), and both increased by ~40% following exposure to $10^{-4}$ M Iso. * P<0.05, ** P<0.001, compared to baseline (no Iso), one-way ANOVA with Tukey post-hoc test.

FIG. 10A includes scanning electron microscopy (SEM) images comparing ultrastructural features of decellularized human left ventricle myocardial tissue (left) and example pull-spun nanofibrous scaffolds before (middle) and after (right) culture with cardiomyocytes in accordance with an example embodiment.

FIG. 10B includes SEM images of example PCL/gelatin nanofibrous sheets at increasing magnifications. Sheets were pull-spun using 75/25 PCL/gelatin mixtures diluted to 6% in solvent, bristle rotation rate was 30,000 RPM, collector rotation rate was 300 RPM, feed rate was 0.2 mL/minute, and collector distance was 20 cm in accordance with example embodiment.

FIG. 10C includes graphs of X-ray photoelectron spectroscopy analysis of gelatin and solvent content in example PCL/gelatin scaffolds including estimated percentage gelatin (left) and solvent (right) content in polycaprolactone/gelatin nanofibrous scaffolds after soaking in de-ionized water for up to 96 hours.

FIG. 10D includes a graph of Bi-axial tensile elastic moduli of example anisotropic PCL/gelatin scaffolds measured longitudinally (in the direction parallel to the fiber axis), EL=499.7±30.7 kPa, or transverse (in the direction perpendicular to the fiber axis), ET=73.8±9.5 kPa. All values are mean±s.e.m.

FIGS. 11A-11C illustrate the analysis of cardiomyocyte distribution and alignment in example ventricle scaffolds.

FIG. 11A includes images of a comparison of an adult rat left ventricular wall cross-section (top) and a thin-walled tissue-engineered NRVM ventricle wall cross-section (bottom) including immunostaining.

FIG. 11B includes images showing transmural cell distribution in an example tissue-engineered NRVM ventricle that was seeded via the exterior surface. DAPI channel thresholding and nuclei counts provided a cell density estimate of ~580 cells/mm$^2$ with a higher density near the ventricle's exterior surface.

FIG. 11C includes images and graphs cell alignment quantified by orientational order parameter (OOP) that ranges from zero (random organization) to one (perfect alignment) for example tissue-engineered ventricles. Immunostained F-actin were analyzed for OOP. Values of 0.85±0.015 (Cor.4U, N=4 ventricles, 25 fields of view) and 0.084±0.022 (NRVM, N=2 ventricles, 19 fields of view) indicated near-perfect alignment. Values are mean±s.e.m.

FIGS. 12A-12C illustrate pressure-volume measurements obtained by tissue-engineered ventricle catheterization of example ventricles in accordance with some embodiments.

FIG. 12A includes images illustrating experimental setups for ventricle catheterization in a temperature-controlled bath in accordance with some embodiments.

FIG. 12B includes graphs of conductance volume catheter calibration using manufacturer-supplied cuvettes (i) and by manual inflation/deflation of catheterized cell-free scaffolds (ii).

FIG. 12C illustrates exemplary data processing steps including smoothing raw data to remove signal noise and converting measured conductance to volume using calibration factors derived in FIG. 12B used for analysis of catheterization data in accordance with some embodiments.

FIG. 13A includes graphs illustrating example data processing steps including polynomial fits to remove signal drift and Fourier-transformation to produce frequency spectra of ventricle beat rates for tissue-engineered ventricles over defined time intervals.

FIG. 13B includes graphs illustrating the effects of calcium depletion on neonatal rat ventricular myocyte (NRVM) ventricle beat rate. Stable beat rates observed in full culture media (M199) gave way to broad beat rate distributions in calcium-depleted phosphate-buffered saline (PBS).

FIG. 13C illustrates the temperature-dependence of NRVM ventricle beat rate for example tissue-engineered ventricles. Low beat rates on the order of ~0.1 Hz observed in room-temperature Tyrode's solution (top panel) increased to ~2 Hz for temperatures between ~30° C. and ~35° C.

FIG. 13D includes time- and frequency-domain plots of example rat and human tissue-engineered ventricle beat rates in response to isoproterenol stimulation. Volume data (left) were Fourier-transformed to produce single-sided amplitude spectra, |Y(f)|, representing beat rate distributions (middle). Surface plots of |Y(f)| produced beat rate heat maps (right) showing beat rate and stability over a given time period (20 seconds in this case).

DETAILED DESCRIPTION

Figure 1A:
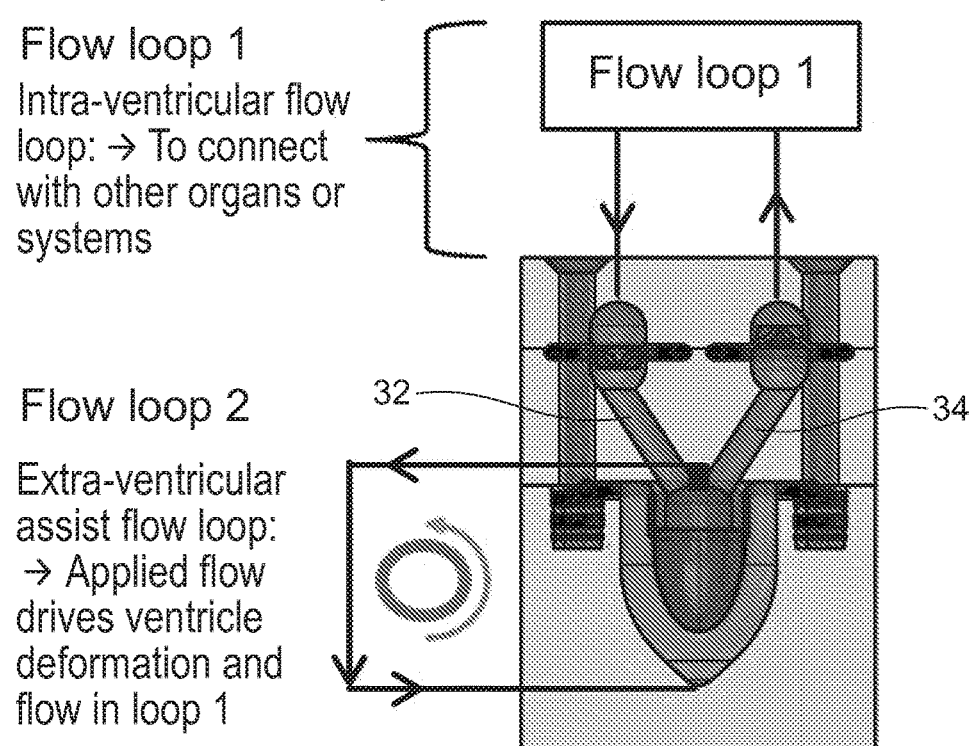
FIG. 1A depicts a front view of system including a housing (e.g., heart bioreactor) holding a hollow tissue structure illustrating flow through the housing in accordance with some embodiments of the present disclosure. Inter- or intra-ventricular flow loops are shown. External pressure supplied via the extra-ventricular flow loop drives ventricle contraction (i.e., ventricular assist), which drives fluid flow through the intraventricular flow loop.

In the following description, it is understood that terms such as "top," "bottom," "middle," "outward," "inward," and the like are words of convenience and are not to be construed as limiting terms. Reference will now be made in detail to embodiments of the disclosure, which are illustrated in the accompanying figures and examples. Referring to the drawings in general, it will be understood that the illustrations are for the purpose of describing particular embodiments of the disclosure and are not intended to limit the same.

Whenever a particular embodiment of the disclosure is said to comprise or consist of at least one element of a group and combinations thereof, it is understood that the embodiment may comprise or consist of any of the elements of the group, either individually or in combination with any of the other elements of that group.

These, and other, aspects of the invention will be better appreciated and understood when considered in conjunction with the following description and the accompanying drawings. The following description, while indicating various embodiments of the invention and numerous specific details thereof, is given by way of illustration and not of limitation. Many substitutions, modifications, additions or rearrangements may be made within the scope of the invention, and the invention includes all such substitutions, modifications, additions or rearrangements.

Referring to FIGS. 1A-2B, some embodiments include a housing 10 configured and dimensioned to receive and engage a hollow tissue (e.g., a ventricle, a heart, a stomach, an intestine, a uterus, a bladder). In some embodiments, the housing is configured and dimensioned to assist with ventricular flow (e.g., testing, preparation/fabrication). The housing 10 defines a fluid chamber 22. The housing also defines a first pair of flow channels 32, 34 fluidly coupled to the fluid chamber 22 and a second pair of flow channels 26, 36 fluidly coupled to the fluid chamber. The housing is configured and dimensioned to receive and engage a hollow tissue structure 100 within the fluid chamber 22 to fluidly couple the first pair of flow channels 32, 34 via a first flow path through an interior of the hollow tissue structure and to fluidly couple the second pair of flow channels 26, 36 via a second flow path extending between an exterior of the hollow tissue structure 100 and a surface of the fluid chamber 22 at least partially surrounding the hollow tissue structure 100. With this configuration a change in a fluid pressure differential between a first fluid in the first flow path and a second fluid in the second flow path deflects at least a portion of the hollow tissue structure 100 causing a change in flow of the first fluid through the first pair of flow channels 32, 34 or a change in flow of the second fluid through the second pair of flow channels 26, 36 as explained in greater detail below.

Housing 10 may include one or more components that in combination define a first surface, a second surface and sidewalls, the first and second surfaces are connected by the sidewalls. Housing 10 may include one or more features that are in communication (e.g., fluid) with features internal to, external to, or partially internal to and partially external to housing 10.

In a non-limiting example, housing 10 may include at least two separable components that, when assembled, create a semi-permanent assembly in fluid communication. Housing 10 may include more or less components, for example, three, four or five components.

In an exemplary embodiment, housing 10 includes three separable components. Housing 10 includes first component (e.g., bottom component) 12, second component (e.g., middle component) 14 and third component (e.g., top component) 16. Bottom component 12, middle component 14 and top component 16 may be positioned directly/indirectly in relation to each other. Although housing 10 is depicted with an upper component, a middle component, and a lower component, one of ordinary skill in the art in view of the present disclosure will appreciate that in some embodiments, the top component and the middle component could be formed as one combined component, or the housing may include more and/or different component portions.

Bottom component 12 is defined by top surface 18 and bottom surface 20, which are connected by of sidewalls. Bottom component 12 defines, in part, fluid chamber 22 with an internal surface 23 of the fluid chamber 22 extending as a cavity from opening 24 of top surface 18 towards bottom surface 20. Fluid chamber 22 is configured and dimensioned to receive hollow tissue structure 100 (e.g., a ventricle, a heart, a stomach, an intestine, a uterus, a bladder). Fluid chamber 22 is in fluid communication with a first pair of flow channels 32, 34 and a second pair of flow channels 26, 36. In some embodiments, a bottom flow channel 26 of the second pair of flow channels is defined, at least in part, by the bottom portion 12. In some embodiments, top surface 18 of bottom component 12 is configured and dimensioned to receive a sealing element 106 (e.g., an O-ring). Sealing element 106 is positioned to surround and seal opening 24 and fluid chamber 22 to middle portion 14.

Middle component 14 is defined by top surface 28 and bottom surface 30, which are connected by a plurality of sidewalls. Middle component 14 defines, in part, fluid chamber 22. Middle component 14 and bottom component 12 define fluid chamber 22. Middle component 14 further defines, at least in part, the first pair of flow channels 32, 34 and defines the upper flow channel 36 of the second pair of flow channels, each of which are in fluid communication with fluid chamber 22. Middle component 14 is configured to sealably engage with bottom component 12 so as to seal opening 24 and fluid chamber 22. Middle component 14 may be configured and dimensioned to directly/indirectly engage with hollow tissue structure 100. In an exemplary embodiment, hollow tissue structure 100 is directly or indirectly engaged with bottom surface 30 of middle component 14 and extends outwardly from middle component 14. In some embodiments, hollow tissue structure 100 extends outwardly from middle component 14 such that upon assembly of middle component 14 with bottom component 12, hollow tissue structure 100 is received and at least partially surrounded by fluid chamber 22.

Top component 16 is defined by top surface 38 and bottom surface 40, which are connected by a plurality of sidewalls. Top component 16 defines, at least in part, the first pair of flow channels 32, 34, which are in fluid communication with fluid chamber 22. Top component 16 is configured to sealably engage with middle component 14 so as to seal openings 35. Top component 16 and middle component 14 may be configured and dimensioned to directly/indirectly engage with one or more optional valves 102. In an exemplary embodiment, at least two valves 102 are in fluid communication with the first pair of flow channels 32, 34 in accordance with some embodiments.

In an exemplary embodiment, housing 10 includes bottom component 12, middle component 14 and top component 16 in direct/indirect relation to another. For example, bottom component 12 is in direct/indirect relation to middle component 14 and middle component 14 is also in direct/indirect relation to top component 16. Hollow tissue structure 100 is directly/indirectly engaged with middle component 14 such that the first pair of flow channels 32, 34 are fluidly coupled to an interior portion of hollow tissue structure 100. Hollow tissue structure 100 may be directly/indirectly supported, in part, by flow channels 32, 34. In some embodiments, middle component 14 may be sealably engaged with bottom component 12 with o-ring 106 so as to seal the first pair of flow channels 32, 34, the second pair of flow channels 26, 36 and flow chamber 22. Valve 102 may be positioned within opening 35 of flow channels 32, 34 to direct flow. In some embodiments, middle component 14 may also be sealably engaged with top component 16 with o-rings 104 so as to seal flow channels 32, 34. In some embodiments, the system or housing 10 may further include may further include fittings 108 for flow channels 26, 32, 34, 36. Bottom component 12, middle component 14 and top component 16 may be temporarily or semi-permanently engaged with each other. Middle component 14 and top component 16 may be temporarily, permanently, or semi-permanently attached to or engaged with each other. Bottom component 12, middle component 14 and top component 16 may include features for engaging each other. Bottom component 12, middle component 14 and top component 16 may be engaged by one or more fasteners 44. In some embodiments fasteners 44 engages with holes 42 that extends at least partially through bottom component 12, middle component 14 and top component 16.

Figures 1B, 1C:
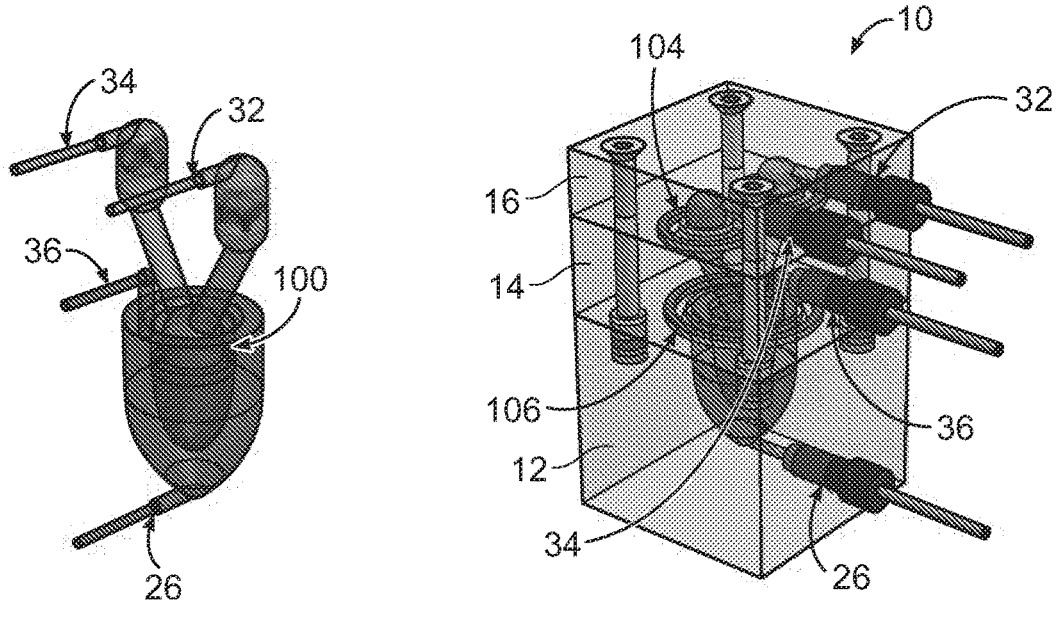
FIG. 1B depicts a perspective view of fluid flow through the housing and hollow tissue structure of FIG. 1A with the housing itself omitted for illustrative purposes.
FIG. 1C depicts a perspective view of the system illustrating fluid couplings to a first pair of flow channels and fluid couplings to a second pair of fluid channels of the channels in accordance with some embodiments.
Figure 2C:
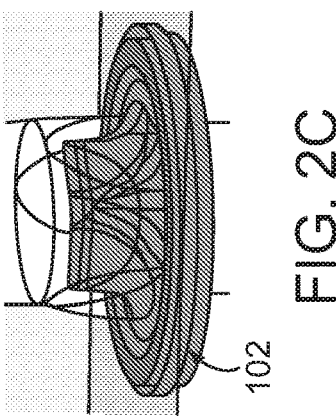
FIG. 2C depicts a perspective view of a flow valve for use with some systems in accordance with some embodiments of the present disclosure.
Figure 2B:
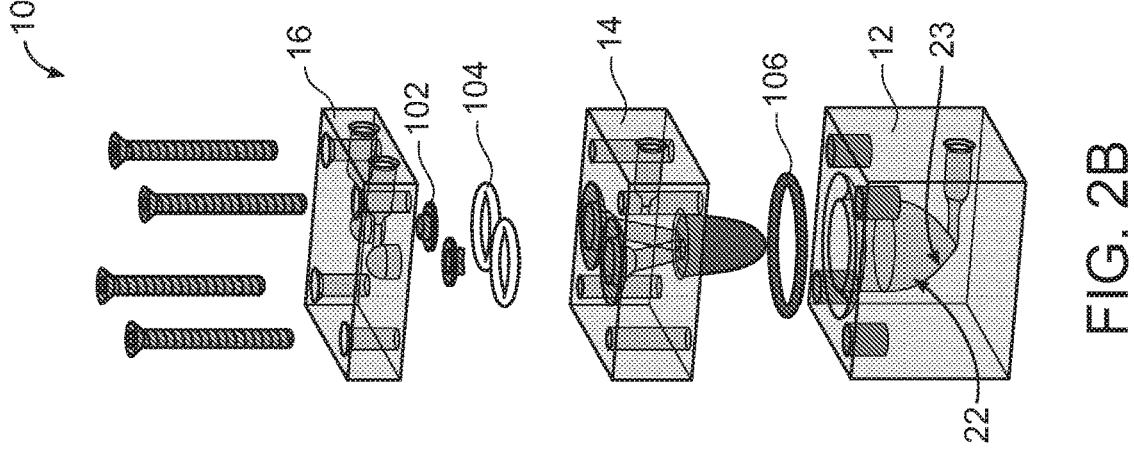
FIG. 2B depicts a perspective exploded view the system of FIG. 2A.
Figure 2A:
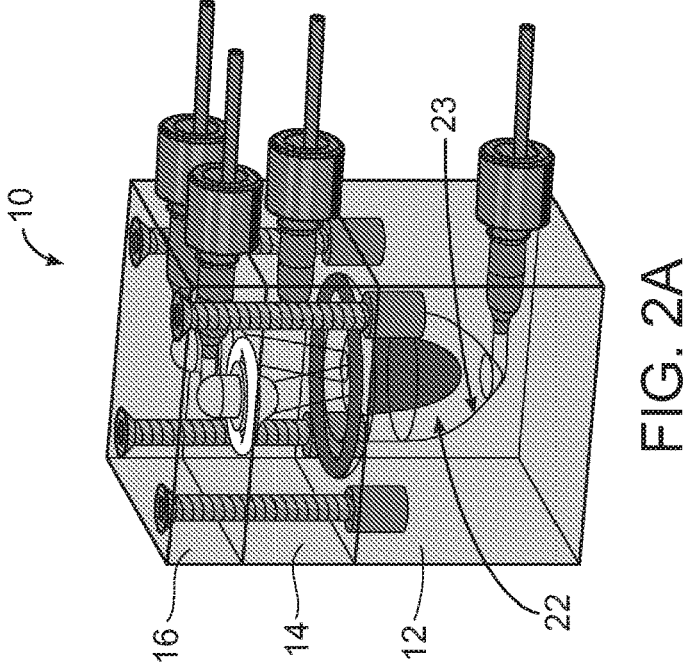
FIG. 2A depicts a perspective view of a system including a housing holding a hollow tissue structure sealing elements in accordance with some embodiments of the present disclosure.
Figure 3A:
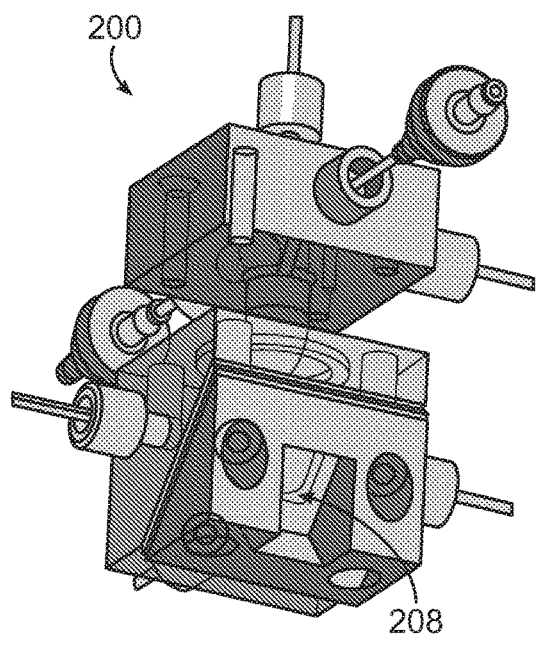
FIG. 3A depicts an exploded view of system including a housing that enables ultrasound imaging through an inserted window in accordance with some embodiments. The system may used as a "heart bioreactor" (HBR) system.
Figure 3B:
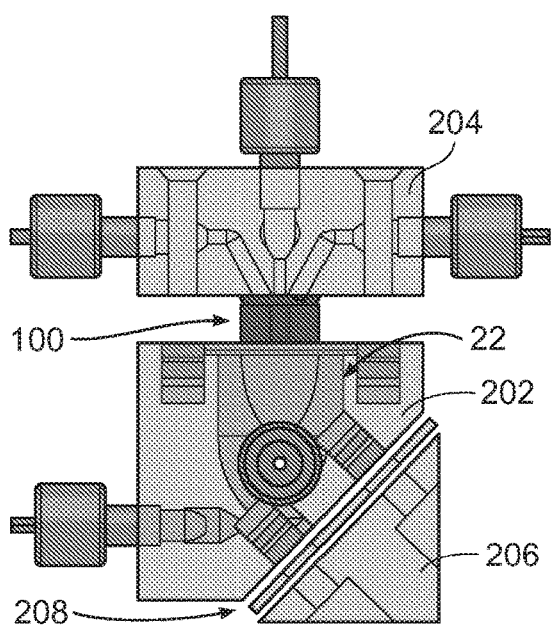
FIG. 3B depicts a side view of the housing of FIG. 3A including an inserted window that enables ultrasound imaging through the window in accordance with some embodiments.
Figure 3C:
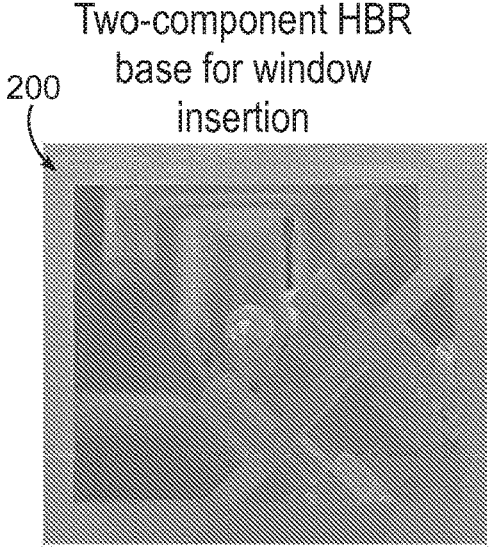
FIG. 3C is an image of a side view of components of an example base manufactured for the housing depicted in FIGS. 3A and 3B.
Figure 3D:
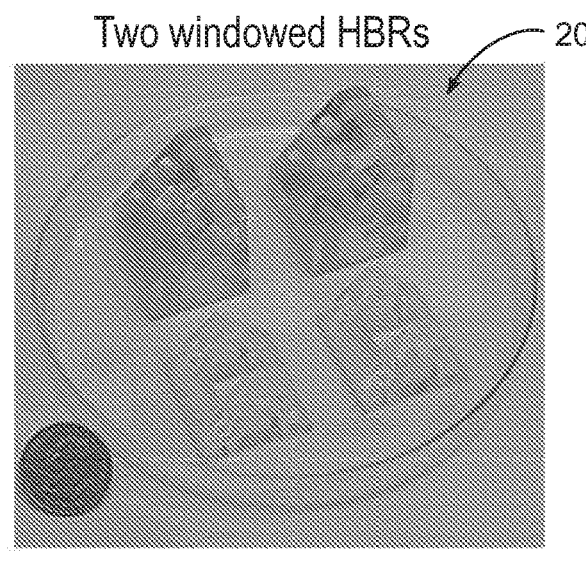
FIG. 3D is an image of two disassembled example housings manufactured based on the design shown in FIGS. 3A and 3B that enables ultrasound imaging through an inserted window, according to some embodiments of the present disclosure.

With specific reference to FIGS. 1A through 1E, a flow loop schematic of hollow tissue structure 100 positioned within housing 10 is depicted. FIG. 1C illustrates the flow of liquids without showing the housing structure for illustrative purposes. The first pair of flow channels ("flow loop 1") is fluidly connected to organs or other systems. Incoming flow of a first fluid travels through a first flow path, which includes, in part, flow channel 32, an interior portion of hollow tissue structure 100 and flow channel 34. As mentioned above, optional flow valves 102 may be associated with flow channels 26, 32, 34, 36. Optional flow valves 102 may be one-way flow valves so as to limit flow to the direction outlined herein. Optional flow valves 102 may control the flow of fluid through one or more flow channels 26, 32, 34, 36. In some embodiments, a system including the housing 10 may also include at least one sensor (not shown) associated with the first flow path. In some embodiments, the at least one sensor may be in direct/indirect contact with hollow tissue structure 100. In some embodiments, the second pair of flow channels ("flow loop 2") may be fluidly connected to a pressurizer (e.g., a pump) that pressurizes or controls fluid pressure in a second fluid that travels through a second flow path, which includes, in part, flow channel 26, flow chamber 22 and flow channel 36. The second flow path may further include at least one sensor. One or more of the fluids associated with the first flow path and the second flow path may be recirculated such that the one or more fluids are in a closed loop configuration. The first fluid and the second fluid may be different fluids or may be similar fluids. For ease of discussion, housing 10 is hidden from the top right image of FIG. 1A so as to only show the first and second flow paths.

In an exemplary embodiment, housing 10 is configured to receive and engage hollow tissue structure 100 within fluid chamber 22 to fluidly couple the first pair of flow channels 32, 34 via a first flow path through an interior of hollow tissue structure 100 and to fluidly couple the second pair of flow channels 26, 36 via a second flow path extending between an exterior of hollow tissue structure 100 and a surface of fluid chamber 22 at least partially surrounding hollow tissue structure 100 such that a change in a fluid pressure differential between a first fluid in the first flow path and a second fluid in the second flow path deflects at least a portion of hollow tissue structure 100 causing a change in flow of the first fluid through the first pair of flow channels 32, 34 or a change in flow of the second fluid through the second pair of flow channels 26, 36. Optionally, a pressurizer may be used to pressurize the second fluid in the second flow path to force the first fluid through the first flow path.

In another exemplary embodiment, as depicted in FIGS. 3A-3D, housing 200 may be configured and dimensioned to assist with ventricular flow (e.g., testing, preparation/fabrication), as described above. Housing 200 may include bottom component 202 and top component 204, which are in direct/indirect contact with each other. Bottom component 202 and top component 204 may be sealably engaged so as to seal hollow tissue structure 100 at least partially within fluid chamber 22, as described above. Housing 200 may further include a window that enables imaging therethrough. Window 208 may enable imaging of the first fluid path, the second fluid path, hollow tissue structure 100, fluid chamber 22, and/or any combination thereof. Window 208 may be fabricated into viewing component 206, which may be detachably positioned with respect to bottom component 202. Window 208 may be fabricated from a transparent material. Window 208 may be fabricated from a material that is transparent to ultrasound (e.g., silicone). Housing 200 may further include at least one sensor positioned in close proximity to the first fluid path and/or the second fluid path.

In some embodiments, a system includes a housing as described herein in combination with a hollow tissue structure. The hollow tissue structure may be disposed in the housing, or provided separately and later disposed in the housing.

In some embodiments, the hollow tissue structure may include a population of cells. The population of cells may form an anisotropic hollow tissue structure. The hollow tissue structure including the population of cells may be a natural hollow tissue structure (e.g., a ventricle, a heart, a stomach, an intestine, a uterus, or a bladder). In some embodiments, the disclosed natural hollow tissue structure may be a diseased tissue structure (e.g., an arrhythmic heart). The hollow tissue structure including the population of cells may be an engineered tissue structure (e.g., a ventricle, a heart, a stomach, an intestine, a uterus, or a bladder). In some embodiments, the disclosed engineered tissue structure may be a diseased tissue structure (e.g., an arrhythmic ventricle).

The population of cells may be selected from the group including normal cells, abnormal cells, normal cells derived from embryonic stem cells or induced pluripotent stem cells, and diseased cells derived from embryonic stem cells or induced pluripotent stem cells, and combinations thereof. The population of cells may further include at least one of vascular smooth muscle cells, cardiac myocytes, skeletal muscle cells, uterine smooth muscle cells, intestinal smooth muscle cells, myofibroblasts, airway smooth muscle cells, osteoblasts, myoblasts, neuroblasts, fibroblasts, glioblasts, germ cells, hepatocytes, chondrocytes, keratinocytes, connective tissue cells, glial cells, epithelial cells, endothelial cells, vascular endothelial cells, hormone-secreting cells, neural cells, and cells that will differentiate into muscle cells.

In some embodiments, the hollow tissue structure may be fabricated from micron-dimension, submicron dimension or nanometer dimension fiber scaffolds.

Any suitable method can be used to prepare the micron-dimension, submicron dimension or nanometer dimension polymeric fiber scaffolds. For example, a method for generating the polymeric fiber scaffolds can include configuring micron, submicron or nanometer dimension polymeric fibers in a desired shape using a collection device, a mandrel or a mandrel assembly.

In one embodiment, suitable polymeric fiber scaffolds can be formed by ejecting a polymer solution from a reservoir onto a rotating mandrel or mandrel assembly, e.g., an ellipsoidal mandrel. In exemplary embodiments, rotary jet spinning (RJS) can be used to create the polymeric fiber scaffolds. Suitable RJS devices and uses of the devices for fabricating the polymeric fiber scaffolds are described in U.S. Patent Publication No. 2012/0135448, U.S. Patent Publication No. 2013/0312638, U.S. Patent Publication No. 2014/0322515, the entire contents of each of which are incorporated in their entirety by reference.

Figures 6A, 6B:
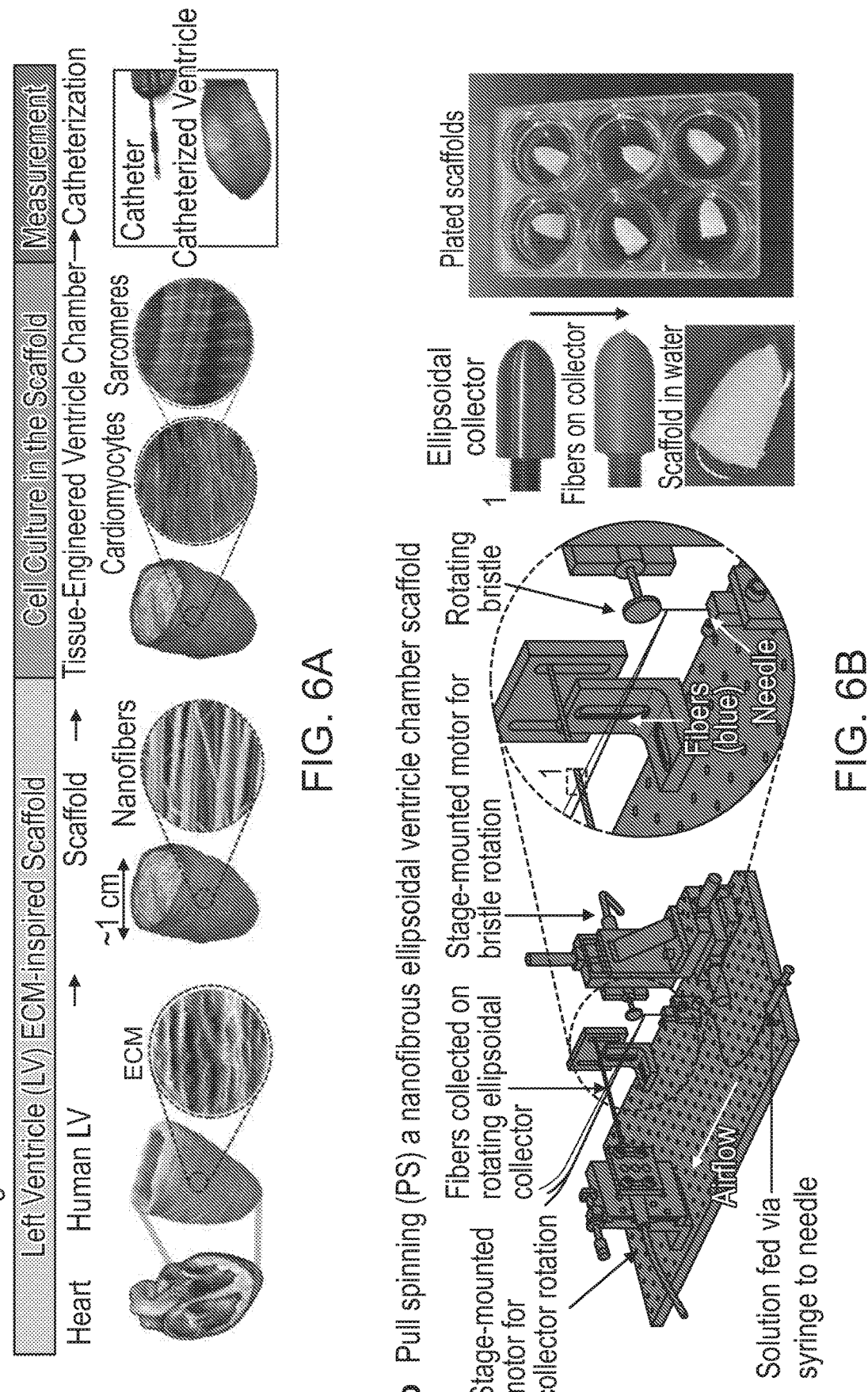
FIGS. 6A-6D illustrate how some example tissue-engineered ventricles recapitulate key structural and functional aspects of natural ventricles in accordance with some embodiments.
Figure 7A:
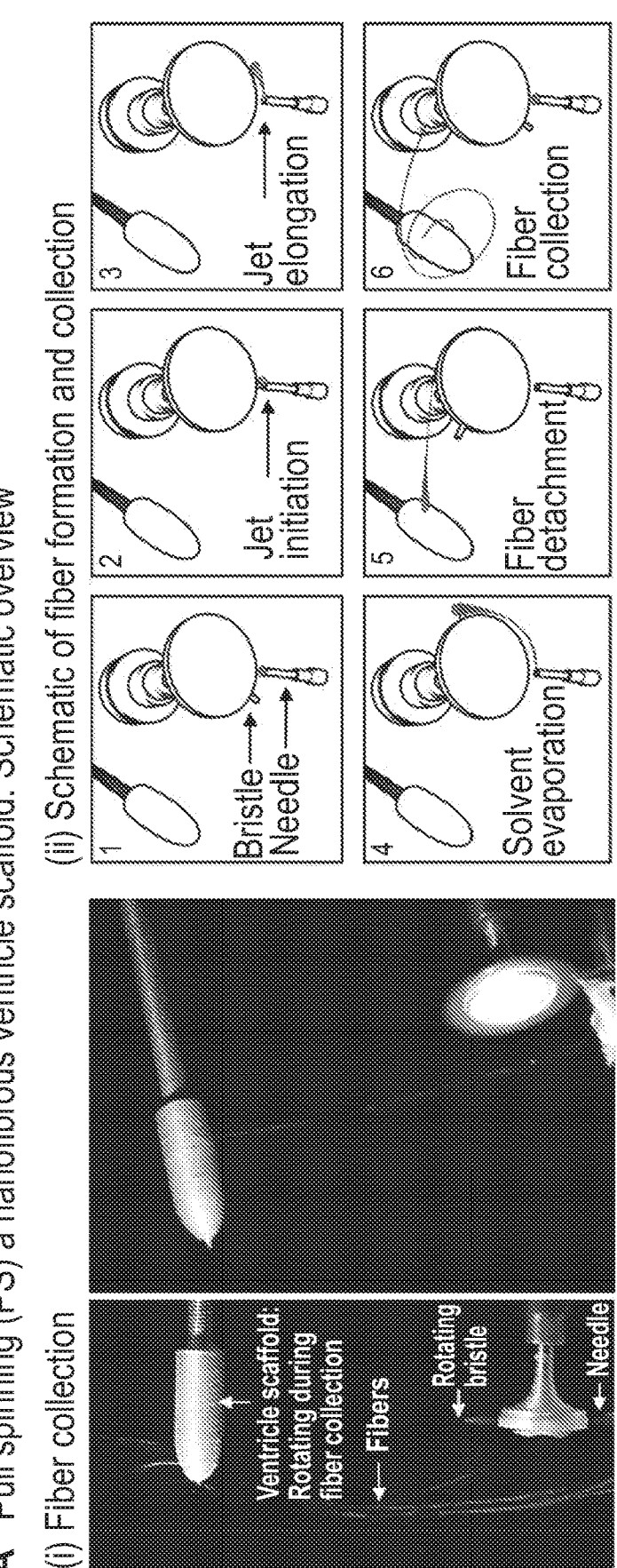
FIGS. 7A-7B illustrate nanofiber production by pull-spinning in accordance with some embodiments.
Figure 7B:
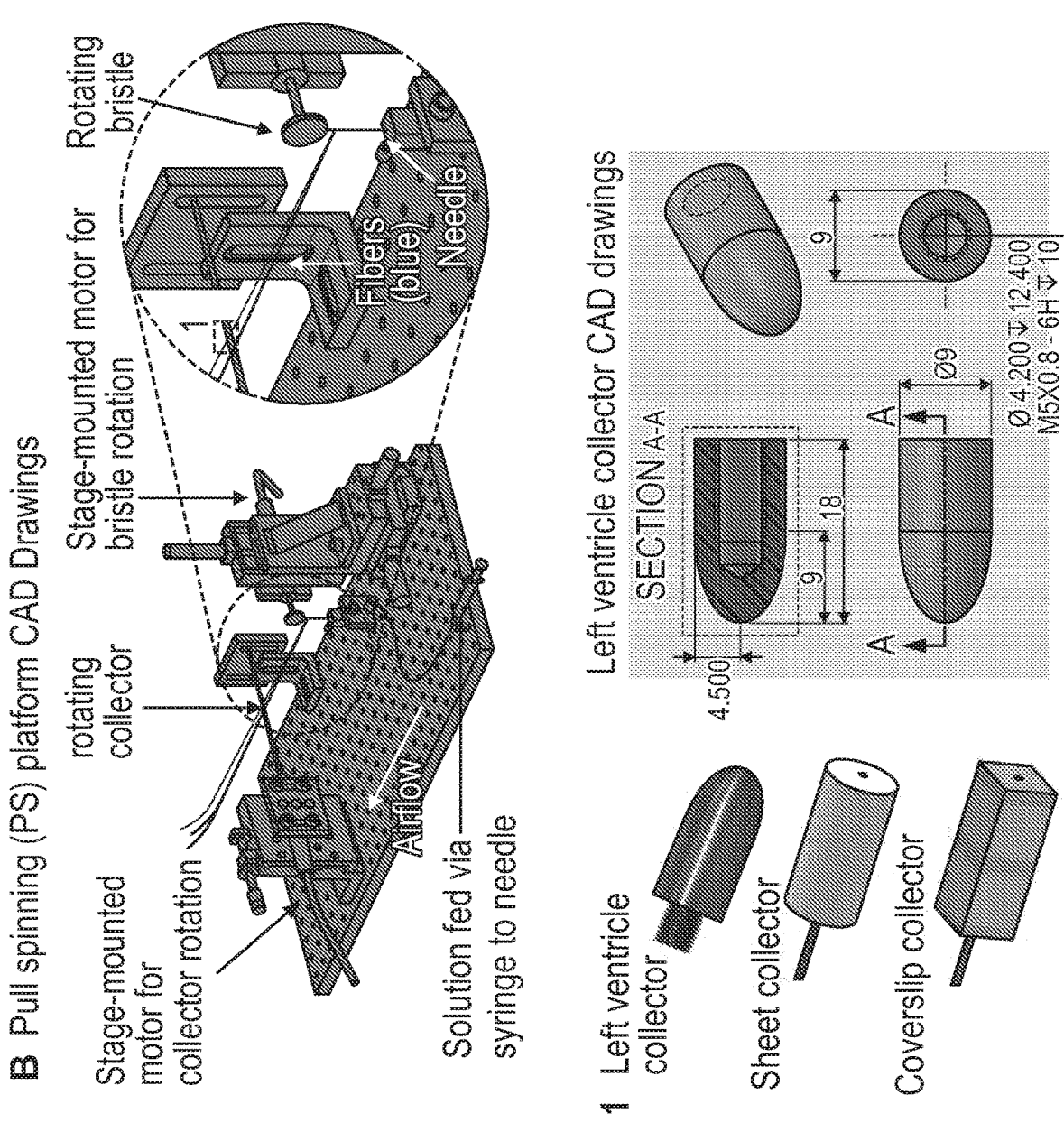
Figure 8A:
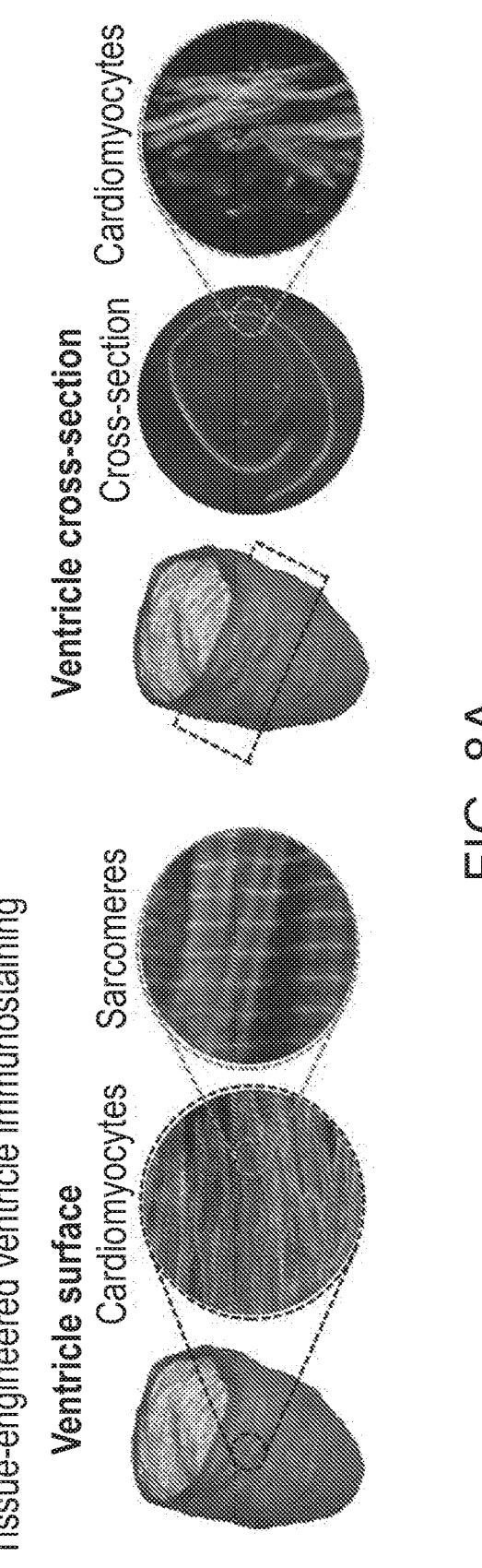
FIGS. 8A-8C illustrate structure of the produced example tissue-engineered ventricles using immunostaining.
Figure 8B:
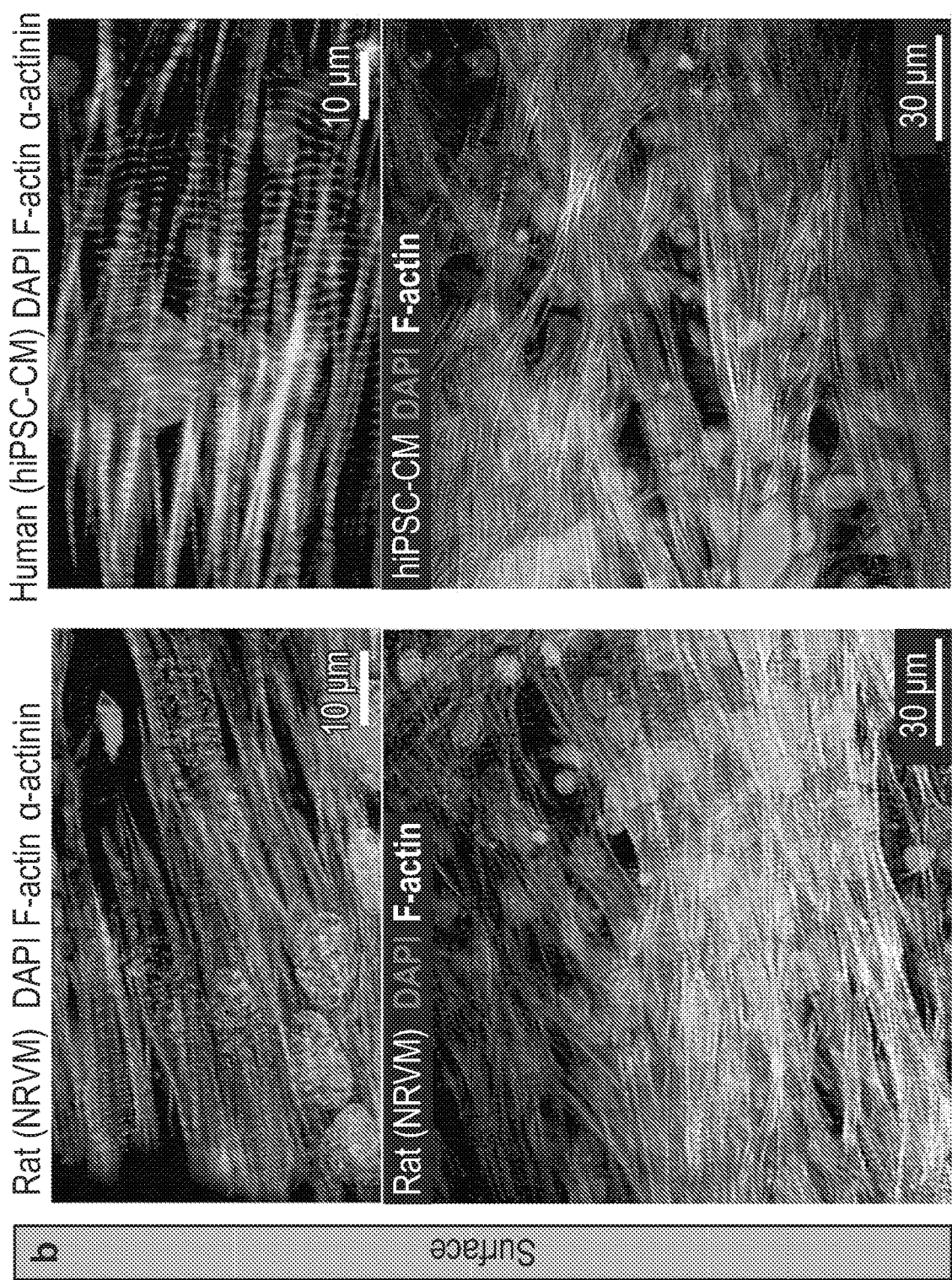
Figure 8C:
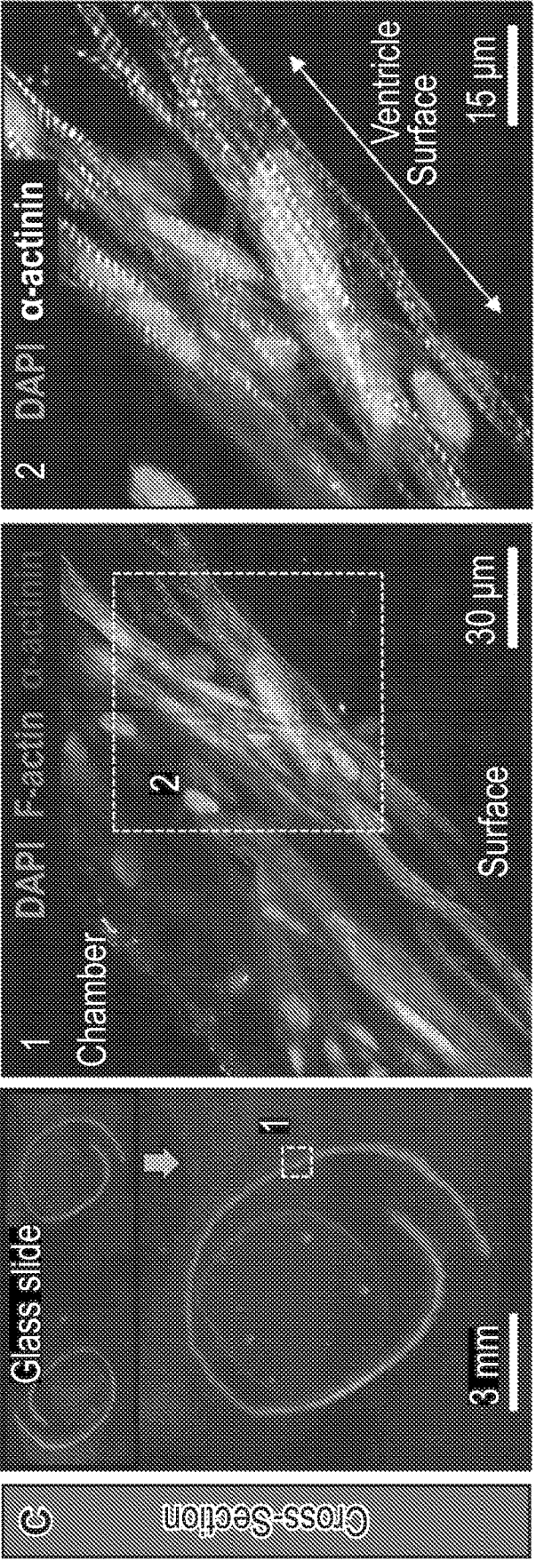

In other exemplary embodiments, the polymeric fibers can be flung using a pull spinning technique onto a collection device, such as a mandrel or a mandrel assembly, e.g., an ellipsoidal mandrel. In one embodiment, suitable polymeric fiber scaffolds can be formed by flinging a polymer solution from a reservoir onto a rotating mandrel or mandrel assembly. Suitable pull spinning devices and uses of the devices for fabricating the non-woven polymeric fiber sheets are described in U.S. Patent Publication No. 2014/0322515, the entire contents of which are incorporated in its entirety by reference, and an exemplary device and method of preparing the suitable polymeric fiber scaffolds are depicted in FIGS. 6B and 7B.

The hollow tissue structures comprising micron-dimension, submicron dimension or nanometer dimension polymeric fiber scaffolds prepared as described above may be seeded with a population of cells to fabricate the engineered hollow tissue structures of the invention.

Accordingly, in some embodiments, a hollow tissue structure comprising micron-dimension, submicron dimension or nanometer dimension polymeric fiber scaffolds is seeded with a plurality cells and cultured in an incubator under physiologic conditions (e.g., at 37° C.) until the cells form a functional tissue structure.

Any appropriate cell culture method may be used. The seeding density of the cells will vary depending on the cell size and cell type, but can easily be determined by methods known in the art. In one embodiment, cells are seeded at a density of between about $1 \times 10^5$ to about $6 \times 10^5$ cells/cm$^2$, or at a density of about $1 \times 10^4$, about $2 \times 10^4$, about $3 \times 10^4$, about $4 \times 10^4$, about $5 \times 10^4$, about $6 \times 10^4$, about $7 \times 10^4$, about $8 \times 10^4$, about $9 \times 10^4$, about $1 \times 10^5$, about $1.5 \times 10^5$, about $2 \times 10^5$, about $2.5 \times 10^5$, about $3 \times 10^5$, about $3.5 \times 10^5$, about $4 \times 10^5$, about $4.5 \times 10^5$, about $5 \times 10^5$, about $5.5 \times 10^5$, about $6 \times 10^5$, about $6.5 \times 10^5$, about $7 \times 10^5$, about $7.5 \times 10^5$, about $8 \times 10^5$, about $8.5 \times 10^5$, about $9 \times 10^5$, about $9.5 \times 10^5$, about $1 \times 10^6$, about $1.5 \times 10^6$, about $2 \times 10^6$, about $2.5 \times 10^6$, about $3 \times 10^6$, about $3.5 \times 10^6$, about $4 \times 10^6$, about $4.5 \times 10^6$, about $5 \times 10^6$, about $5.5 \times 10^6$, about $6 \times 10^6$, about $6.5 \times 10^6$, about $7 \times 10^6$, about $7.5 \times 10^6$, about $8 \times 10^6$, about $8.5 \times 10^6$, about $9 \times 10^6$, or about $9.5 \times 10^6$. Values and ranges intermediate to the above-recited values and ranges are also contemplated by the present invention.

In some embodiments, a scaffold is contacted with living cells during the fabrication process such that a structure populated with cells or fibers surrounded (partially or totally) with cells are produced. The scaffold may also be contacted with additional agents, such as proteins, nucleotides, lipids, drugs, pharmaceutically active agents, biocidal and antimicrobial agents during the fabrication process such that functional micron, submicron or nanometer dimension polymeric fibers are produced which contain these agents. For example, fibers comprising living cells may be fabricated by providing a polymer and living cells in a solution of cell media at a concentration that maintains cell viability.

Suitable cells for use in the invention may be normal cells, abnormal cells (e.g., those derived from a diseased tissue, or those that are physically or genetically altered to achieve an abnormal or pathological phenotype or function), normal or diseased muscle cells, stem cells (e.g., embryonic stem cells), or induced pluripotent stem cells. Suitable cells include vascular smooth muscle cells, cardiac myocytes, skeletal muscle cells, uterine smooth muscle cells, intestinal smooth muscle cells, myofibroblasts, airway smooth muscle cells, osteoblasts, myoblasts, neuroblasts, fibroblasts, glioblasts, germ cells, hepatocytes, chondrocytes, keratinocytes, connective tissue cells, glial cells, epithelial cells, endothelial cells, vascular endothelial cells, hormone-secreting cells, neural cells, and cells that will differentiate into muscle cells. Such cells may be seeded on the scaffold and cultured to form a functional tissue, such as a functional hollow tissue structure.

Cells for seeding can be cultured in vitro, derived from a natural source, genetically engineered, or produced by any other means. Any natural source of prokaryotic or eukaryotic cells may be used.

The term "progenitor cell" is used herein to refer to cells that have a cellular phenotype that is more primitive (e.g., is at an earlier step along a developmental pathway or progression than is a fully differentiated cell) relative to a cell which it can give rise to by differentiation. Often, progenitor cells also have significant or very high proliferative potential. Progenitor cells can give rise to multiple distinct differentiated cell types or to a single differentiated cell type, depending on the developmental pathway and on the environment in which the cells develop and differentiate.

The term "progenitor cell" is used herein synonymously with "stem cell."

The term "stem cell" as used herein, refers to an undifferentiated cell which is capable of proliferation and giving rise to more progenitor cells having the ability to generate a large number of mother cells that can in turn give rise to differentiated, or differentiable daughter cells. The daughter cells themselves can be induced to proliferate and produce progeny that subsequently differentiate into one or more mature cell types, while also retaining one or more cells with parental developmental potential. The term "stem cell" refers to a subset of progenitors that have the capacity or potential, under particular circumstances, to differentiate to a more specialized or differentiated phenotype, and which retains the capacity, under certain circumstances, to proliferate without substantially differentiating. In one embodiment, the term stem cell refers generally to a naturally occurring mother cell whose descendants (progeny) specialize, often in different directions, by differentiation, e.g., by acquiring completely individual characters, as occurs in progressive diversification of embryonic cells and tissues. Cellular differentiation is a complex process typically occurring through many cell divisions. A differentiated cell may derive from a multipotent cell which itself is derived from a multipotent cell, and so on. While each of these multipotent cells may be considered stem cells, the range of cell types each can give rise to may vary considerably. Some differentiated cells also have the capacity to give rise to cells of greater developmental potential. Such capacity may be natural or may be induced artificially upon treatment with various factors. In many biological instances, stem cells are also "multipotent" because they can produce progeny of more than one distinct cell type, but this is not required for "stem-ness." Self-renewal is the other classical part of the stem cell definition. In theory, self-renewal can occur by either of two major mechanisms. Stem cells may divide asymmetrically, with one daughter retaining the stem state and the other daughter expressing some distinct other specific function and phenotype. Alternatively, some of the stem cells in a population can divide symmetrically into two stems, thus maintaining some stem cells in the population as a whole, while other cells in the population give rise to differentiated progeny only. Formally, it is possible that cells that begin as stem cells might proceed toward a differentiated phenotype, but then "reverse" and re-express the stem cell phenotype, a term often referred to as "dedifferentiation" or "reprogramming" or "retrodifferentiation".

The term "embryonic stem cell" is used to refer to the pluripotent stem cells of the inner cell mass of the embryonic blastocyst (see U.S. Pat. Nos. 5,843,780, 6,200,806, the contents of which are incorporated herein by reference). Such cells can similarly be obtained from the inner cell mass of blastocysts derived from somatic cell nuclear transfer (see, for example, U.S. Pat. Nos. 5,945,577, 5,994,619, 6,235,970, which are incorporated herein by reference). The distinguishing characteristics of an embryonic stem cell define an embryonic stem cell phenotype. Accordingly, a cell has the phenotype of an embryonic stem cell if it possesses one or more of the unique characteristics of an embryonic stem cell such that that cell can be distinguished from other cells. Exemplary distinguishing embryonic stem cell characteristics include, without limitation, gene expression profile, proliferative capacity, differentiation capacity, karyotype, responsiveness to particular culture conditions, and the like.

The term "adult stem cell" or "ASC" is used to refer to any multipotent stem cell derived from non-embryonic tissue, including fetal, juvenile, and adult tissue. Stem cells have been isolated from a wide variety of adult tissues including blood, bone marrow, brain, olfactory epithelium, skin, pancreas, skeletal muscle, and cardiac muscle. Each of these stem cells can be characterized based on gene expression, factor responsiveness, and morphology in culture. Exemplary adult stem cells include neural stem cells, neural crest stem cells, mesenchymal stem cells, hematopoietic stem cells, and pancreatic stem cells.

In one embodiment, progenitor cells suitable for use in the claimed devices and methods are Committed Ventricular Progenitor (CVP) cells as described in PCT Application No. WO 2010/042856, entitled "Tissue Engineered Myocardium and Methods of Productions and Uses Thereof", filed Oct. 9, 2009, the entire contents of which are incorporated herein by reference.

The hollow tissue structures comprising a population of cells and systems of the invention are suitable for use in, among other things, culturing cells or cell clusters, and forming engineered tissue. Such tissue can be useful not only for the production of prosthetic devices and regenerative medicine, but also for investigating tissue developmental biology and disease pathology, as well as in drug discovery and toxicity testing. The hollow tissue structures comprising a population of cells and systems of the invention can also be combined with other substances, such as, therapeutic agents, in order to deliver such substances to the site of application or implantation of the hollow tissue structures.

In one aspect, the hollow tissue structures comprising a population of cells and systems of the invention are useful for screening compounds that modulate a property of the cells contained therein. The methods include providing a hollow tissue structure comprising a population of cells, or system according to the instant invention, contacting the hollow tissue structure and/or the population of cells, device, or system with a test compound, and monitoring a parameter in the absence of the compound (negative control) and in the presence of the compound. A change in the parameter in the presence of the test compound compared to the parameter in absence of the test compound indicates that the test compound is effective in modulating the property.

In one embodiment, the parameter can be growth, division, differentiation, or viability of the cells. Identification of a test compound that modulates the cell property can also be made by evaluating various physiological parameters such as cell morphology, cell structure, cell agglutination, formation of cell clusters, cell size, presence or absence of vesicles/granules, or the like.

In another aspect, the hollow tissue structures comprising a population of cells and systems of the invention are useful for screening compounds that modulate a hollow tissue function. The methods include providing a hollow tissue structure comprising a population of cells or a system as disclosed throughout the present disclosure, contacting the hollow tissue structure and/or the population of cells with a test compound, and determining the effect of the test compound on a hollow tissue function in the presence and absence of the test compound, wherein a modulation of the hollow tissue function in the presence of the test compound as compared to the hollow tissue function in the absence of the test compound indicates that the test compound modulates a hollow tissue function, thereby identifying a compound that modulates a hollow tissue function.

In another aspect, the hollow tissue structures comprising a population of cells and systems of the invention are useful for screening compounds useful for treating a hollow tissue disease. The methods include providing a hollow tissue structure comprising a population of cells or a system as disclosed throughout the present disclosure, contacting the hollow tissue structure and/or the population of cells with a test compound, and determining the effect of the test compound on a hollow tissue function in the presence and absence of the test compound, wherein a modulation of the hollow tissue function in the presence of the test compound as compared to the hollow tissue function in the absence of the test compound indicates that the test compound modulates a hollow tissue function, thereby identifying a compound useful for treating or preventing a hollow tissue disease.

In some embodiments, the tissue function may be a biomechanical activity. The biomechanical activity may be one or more of contractility, cell stress, cell swelling, and rigidity. The biomechanical activity may also be one or more of stem cell activation, stem cell maturation, tissue morphogenesis, and tissue remodeling. In other embodiments, the tissue function may be an electrophysiological activity. The electrophysiological activity may be a voltage parameter selected from the group including action potential, action potential duration (APD), conduction velocity (CV), refractory period, wavelength, restitution, bradycardia, tachycardia, reentrant arrhythmia, and/or a calcium flux parameter, e.g., intracellular calcium transient, transient amplitude, rise time (contraction), decay time (relaxation), total area under the transient (force), restitution, focal and spontaneous calcium release.

As used herein, the various forms of the term "modulate" are intended to include stimulation (e.g., increasing or upregulating a particular response or activity) and inhibition (e.g., decreasing or downregulating a particular response or activity).

As used herein, the term "contacting" (e.g., contacting a scaffold including pancreatic islet cells or adipocytes with a test compound) is intended to include any form of interaction (e.g., direct or indirect interaction) of a test compound and a scaffold or cells. The term contacting includes incubating a compound and scaffold or tissue together (e.g., adding the test compound to scaffold including pancreatic islet cells or adipocytes in culture).

Test compounds can be any agents including chemical agents (such as toxins), small molecules, pharmaceuticals, peptides, proteins (such as antibodies, cytokines, enzymes, and the like), nanoparticles, and nucleic acids, including gene medicines and introduced genes, which may encode therapeutic agents, such as proteins, antisense agents (i.e., nucleic acids comprising a sequence complementary to a target RNA expressed in a target cell type, such as RNAi or siRNA), ribozymes, and the like.

The hollow tissue structure and/or the population of cells can be contacted with a test compound by any suitable means. For example, the test compound can be added drop-wise onto the surface structure and allowed to diffuse into or otherwise enter the structure, or it can be added to the nutrient medium and allowed to diffuse through the medium.

This invention is further illustrated by the following examples which should not be construed as limiting. The contents of all references, patents and published patent applications cited throughout this application, as well as the Figures, are hereby incorporated by reference.

EXAMPLES

Example 1. Tissue-Engineered Human Ventricles

The following example demonstrates the fabrication of a tissue-engineered functional ventricle and a modular bioreactor platform as well as the use thereof for in situ instrumentation and functional assessment for in vitro cardiology studies.

More specifically, the following example describes determining the minimal essential features of human ventricle structure that can be reliably recapitulated using nanofiber production platforms in order to test if nanofibrous scaffolds are suitable for ventricle chamber tissue engineering. The foregoing example also describes the subsequent fabrication of ellipsoidal thin-walled chambers composed of a nanofibrous synthetic-natural polymer-protein blend and seeding with neonatal rat ventricular myocytes (NRVM) or human induced pluripotent stem cell-derived cardiomyocytes (hiPSC-CM). Synchronous chamber-level contraction was observed for both cell types after 3-5 days of culture in the scaffolds. The resulting tissue-engineered ventricle chambers were sutured to tubing or bioreactor components through which catheter sensors were introduced and stable contraction of both NRVM and hiPSC-CM ventricles permitted time-dependent pressure and volume measurements. Ventricle beat rates showed positive chronotropic responses to isoproterenol exposure, comparable to other assays based on similar cell types. The findings confirm that tissue-engineered ventricle contraction can be monitored by catheter sensors, with implications for preclinical cardiology and regenerative medicine research where human organ models are sought to improve translation of therapeutic strategies.

Materials and Methods

The following materials and methods were used in this Example.

Scaffold Fabrication

Polymer solutions. Ventricle scaffold material precursors were polycaprolactone (PCL; Sigma Aldrich 440744) and gelatin Type A (Sigma Aldrich G2500) dissolved in a solvent, 1,1,1,3,3,3-Hexafluoro-2-propanol (HFIP; Oakwood Chemical 003409). All materials were used as received without further modifications. A mixture of 75% PCL and 25% gelatin was dissolved at 6% weight/volume in HFIP and stirred for at least 12 hours to ensure homogeneous mixing.

Ventricle scaffold fabrication. Ventricle scaffolds were produced by pull spinning (PS; FIGS. 6B, 7A, and 7B) PCL/gelatin nanofibers onto ellipsoidal collection mandrels (half-ellipsoid with radii: a=b=4.5 mm, c=9 mm; FIG. 7B) (Deravi, L. F. et al. *Macromolecular Materials and Engineering* 302, 2017). Devices and Methods suitable for pull-spinning polymeric fibers are described in, for example, U.S. Pat. No. 9,738,046, the entire contents of which are incorporated herein by reference. Briefly, pull spinning incorporates a high-speed (up to 45,000 RPM) rotating bristle that dips into a fixed, continuous polymer source and pulls the polymer column into an anisotropic network of non-woven nanofibers. The solution was injected through a needle (18G flat tip; BD Biosciences) at a rate of 0.2 mL/min for a total duration of 5 min. Bristle rotation rate was 30,000 RPM. Ventricle mandrels were connected to a DeWALT DC 720½" cordless drill driver rotation operating at 300 RPM and the mandrels were located 20 cm from the polymer source. All PS fabrication was performed within a chemical fume hood and the relative humidity was between 10-20%. Scaffolds were stored in de-ionized water for 48 hours and sterilized by overnight exposure to UV radiation within a tissue culture hood prior to use.

Scaffold Structural and Biochemical Analysis

X-ray Microcomputed Tomography ($\mu$CT). An X-Tek HMXST225 system (Nikon Metrology, Inc.) equipped with a 225 kV microfocus X-ray source with 3 $\mu$m focal spot size was used. An aluminum target and 115 kV accelerating voltage was used. Image acquisition and reconstruction was performed using the following software suites: InspectX (X-ray imaging and CT acquisition), CT Pro 3D (volume reconstruction), VG Studio MAX 2.2 (3D volume visualization, rendering and analysis), and Amira (3D volume visualization, rendering and analysis).

Scanning electron microscopy. All SEM imaging was done using a field emitting electron microscope (FESEM Ultra Plus, Zeiss) at a voltage of 15 kV to image scaffold and tissue fiber alignment. Prior to imaging, all samples were sputter coated with 5 nm of Platinum/Palladium (Pt/Pd) using a Quorum Sputter Coater (EMS 300T D, Quorum Technologies) to reduce charge accumulation and tissue decomposition during imaging. Decellularized human tissue was prepared using a previously published SDS profusion protocol (Guyette, J. P. et al. "Bioengineering human myocardium on native extracellular matrix". *Circ Res* 118, 56-72, 2016) and dehydrated in serial ethanol washes. Dehydrated tissues were then dried using a SAMDRI critical point drier (931 Series SAMDRI, Tousimis) prior to sputter coating to ensure complete removal of interstitial fluids.

Mechanical Testing. To measure elastic modulus, sheets of nanofibrous material were produced (FIGS. 7A-7B and 10A-10C), collected on flat glass coverslips, using the same pull-spinning conditions as for ventricle chamber production. Square samples were laser-cut (10×10 mm) from these sheets and loaded onto 5×5 mm mounting tines for biaxial tensile testing (2.5 N load cells; Biotester, CellScale, Canada). A pre-stress of 5 $\mu$N was applied before running four biaxial preconditioning cycles at 5% strain rate to 20% strain. Using the original dimensions of the nanofibrous samples, the strain-strain curve was then calculated (same strain rate and strain were used as preconditioning). To replicate in vitro conditions, tensile measurements were performed in PBS at 37° C.

X-ray photoelectron spectrometry. A K-Alpha X-ray photoelectron spectrometer and Advantage software (K-Alpha XPS, Thermo Scientific) was used to evaluate fresh-spun and wetted scaffold composition in time. 5×5 mm pieces of 75/25 PCL/Gelatin scaffold were wetted in 1 L of ultra-pure water and stored in an incubator at 37° C. for up to 1 week. Fresh spun and wetted samples removed from the water bath daily were dried for 12 hr under vacuum and their composition evaluated using the XPS system (n=3 scaffold pieces and XPS measurements per time point, 0-7 days). Briefly, each sample was etched for 30 s at 500 eV to remove surface debris and was survey scanned over a 400 square micron spot size. Gelatin content was estimated based upon the measured presence of nitrogen in the sample and the amount of solvent (HFIP) was estimated based upon the measured presence of fluorine, each normalized to the element's percentage within their respective molecule.

Fourier Transform Infrared Spectroscopy (FT-IR). A Bruker FT-IR Microscope (Lumos, Bruker, Billerica, MA) was used in attenuated total reflection (ATR) mode to measure the infrared spectra of the nanofibers. Data plotting was conducted with custom software written in MATLAB (MathWorks, Natick, MA).

Cell and Tissue Culture

Neonatal rat ventricular myocytes (NRVM). NRVM were isolated from 2-day old neonatal Sprague-Dawley using published methods (Feinberg, A. W. et al. *Science* 317, 1366-1370, 2007). Cells were seeded at a density of 3 million cells per ventricle following procedures described below. Standard culture media were used (M199 culture medium supplemented with 0.1 mM MEM nonessential amino acids, 10% heat-inactivated FBS, 10 mM HEPES, 3.5 g/L glucose, 2 mM L-glutamine, 2 mg/L vitamin B-12, and 50 U/ml penicillin). Samples were incubated under standard conditions at 37° C. and 5% CO2. At 48 h post seeding the media was exchanged with maintenance media (M199 media supplemented as above but with 2% FBS) and was exchanged again every 48 h until use.

Human induced pluripotent stem cell-derived cardiomyocytes (hiPSC-CM). hiPSC-CMs were acquired commercially (Lot numbers CB169CL_V1_1M, CB301_CL_v1_1M, CB319CL_V1_1M, CB324CL_V1_1M, CB331CL_V1_4M; Axiogenesis, Cologne, Germany) and cultured according to manufacturer's instructions with slight modifications. Briefly, for each cryovial containing 1 million viable hiPSC-CMs, 3 wells of a 6 well tissue culture plate were coated with 0.01 µg/mL fibronectin (FN) (BD Biosciences, Bedford, MA) for 4 hours in a 37° C. incubator. According to the manufacturer, Cor.4U cells show typical ventricular-, atrial- and nodal-like action potentials, demonstrating the different Cor.4U subtypes. Cor.4U comprises 60% ventricular cells. Cryovials of Cor.4U hiPSC-CMs were quickly thawed in a 37° C. water bath, re-suspended in 10 mL of complete culture medium provided by the manufacturer supplemented with 5 µL of 10 mg/mL puromycin, and cultured in FN-coated tissue culture plates at 37° C. and 5% $CO_2$ for 48 hours to eliminate undifferentiated stem cells from the culture. After 48 hours, cells were dissociated with 0.25% trypsin and seeded onto ventricular scaffolds.

Ventricle Seeding. Ventricle scaffolds were sterilized by exposure to ultraviolet radiation in a biosafety hood overnight and then incubated with 100 µg/mL fibronectin (Human natural fibronectin, BD Biosciences) in PBS for 90 minutes. Cells were then transferred to the scaffold at high density (0.5 mL full media containing 3M cells) and incubated (37° C., 5% $CO_2$) for 90 minutes. Two mL of full media was then added to each well and incubated overnight. Ventricles were then transferred to larger wells, each well containing 5 mL full media and one ventricle, with media refreshed every 48 hours until use.

Histochemical Staining

Cardiomyocyte infiltration and orientation within tissue-engineered ventricles was visualized by fluorescent staining of actin and sarcomeres. Staining for F-actin fibers and sarcomeric α-actinin was performed as previously described (Feinberg, A. W. et al. *Science* 317, 1366-1370, 2007). Briefly, washed samples were fixed in 4% paraformaldehyde for 20 minutes. To prepare ventricle cross-sections, gelatin molds were first casted of the ventricular volume by pouring dissolved gelatin (20% w/v) into ventricle-shaped molds, followed by cooling and removal of the solid gelatin from the mold. The fixed ventricles were then pulled over the gelatin mold to ensure that thin-walled ventricles maintained an ellipsoidal shape during cryopreservation. Ventricles (with gelatin interior) were stored in PBS+30% sucrose solution overnight at 4° C., transferred to 50% sucrose/50% OCT for 24 h at 4° C. They were then transferred to cryosectioning containers in 100% OCT and stored at 4° C. for 48 h. Samples were frozen by partial immersion in 2-methylbutane which was, itself, partially immersed in liquid nitrogen. Frozen ventricles were stored at −80° C. until cryosectioning by microtome (Leica). 30 µm-thick cross-sections were obtained and transferred to glass microscope slides (Superfrost microscope slides, Sigma) and maintained at room temperature for 2 h prior to storage at −80° C. until staining.

Staining and Imaging

Ventricle surfaces or cross-sections were permeabilized in 0.5% Triton-X100 for 20 minutes in PBS at 37° C., followed by 2-h incubation with 1:200 dilutions of mouse anti-sarcomeric α-actinin monoclonal primary antibody (Sigma-Aldrich, clone EA-53, catalog number A7811-11UL). Samples were then washed and concurrently incubated with 1:200 dilutions of DAPI (Sigma-Aldrich), phalloidin conjugated to Alexa-Fluor 488 (Invitrogen, Carlsbad, CA 92008, USA) and goat anti-mouse secondary antibody conjugated to tetramethylrhodamine for 2 h at room temperature. Imaging was performed using a Zeiss LSM 5 LIVE confocal microscope with a Plan-Neofluar 40×/1.3 oil objective. Cell alignment was quantified using a metric known as the orientational order parameter (OOP) that ranges from zero (random organization) to one (perfect alignment) (Feinberg, A. W. et al. *Biomaterials* 33, 5732-5741, 2012; and Pasqualini, F. S., et al. Stem Cell Reports 4, 340-347, 2015), applied to immunostained F-actin.

Optical Mapping Experiments

Calcium propagation was monitored using a modified tandem-lens macroscope (Scimedia, Costa Mesa, CA) equipped with a high speed camera (MiCAM Ultima, Scimedia, Costa Mesa, CA), a plan APO 0.63× objective, a collimator (Lumencor, Beaverton, OR) and a 200 mW Mercury lamp (X-Cite exacte, Lumen Dynamics, Canada). After 2 weeks of culture in vitro, ventricles were incubated with 2 µM Rhod-2 (Invitrogen, Carlsbad, CA) for 30 min at 37° C., rinsed, and incubated in dye-free media for an additional 15 mins at 37° C. prior to recording. The ventricles were then rinsed with Tyrode's buffer. Recordings were acquired at a frame rate of 200 Hz. Electrical field and point simulation was applied using two platinum electrodes (Sigma-Aldrich, St. Louis, MO) with 20 mm and 1 mm spacing, respectively. The point stimulator was located at 0.5-1 mm from the apex of the ventricle with a motorized xy-micromanipulator (Zaber Technologies Inc., Vancouver, British Columbia, Canada). Electrical pulses were generated with 12 V amplitude and 10 ms duration using a pulse generator (MyoPacer Cell Stimulator, IonOptix, Milton, MA). Pacing frequency was 1 Hz for NRVM ventricles and 3 Hz for hiPSC-CM ventricles. Post-processing of data was conducted with custom software written in MATLAB (MathWorks, Natick, MA). A spatial filter with 3×3 pixels was applied to improve the signal-noise ratio. Activation time of point-stimulated ventricle was calculated as the average time to maximum upstroke slope of pulses when continuously at 1 Hz pacing during in a 5 sec recording window.

Pressure-Volume Measurements

Figure 12A:
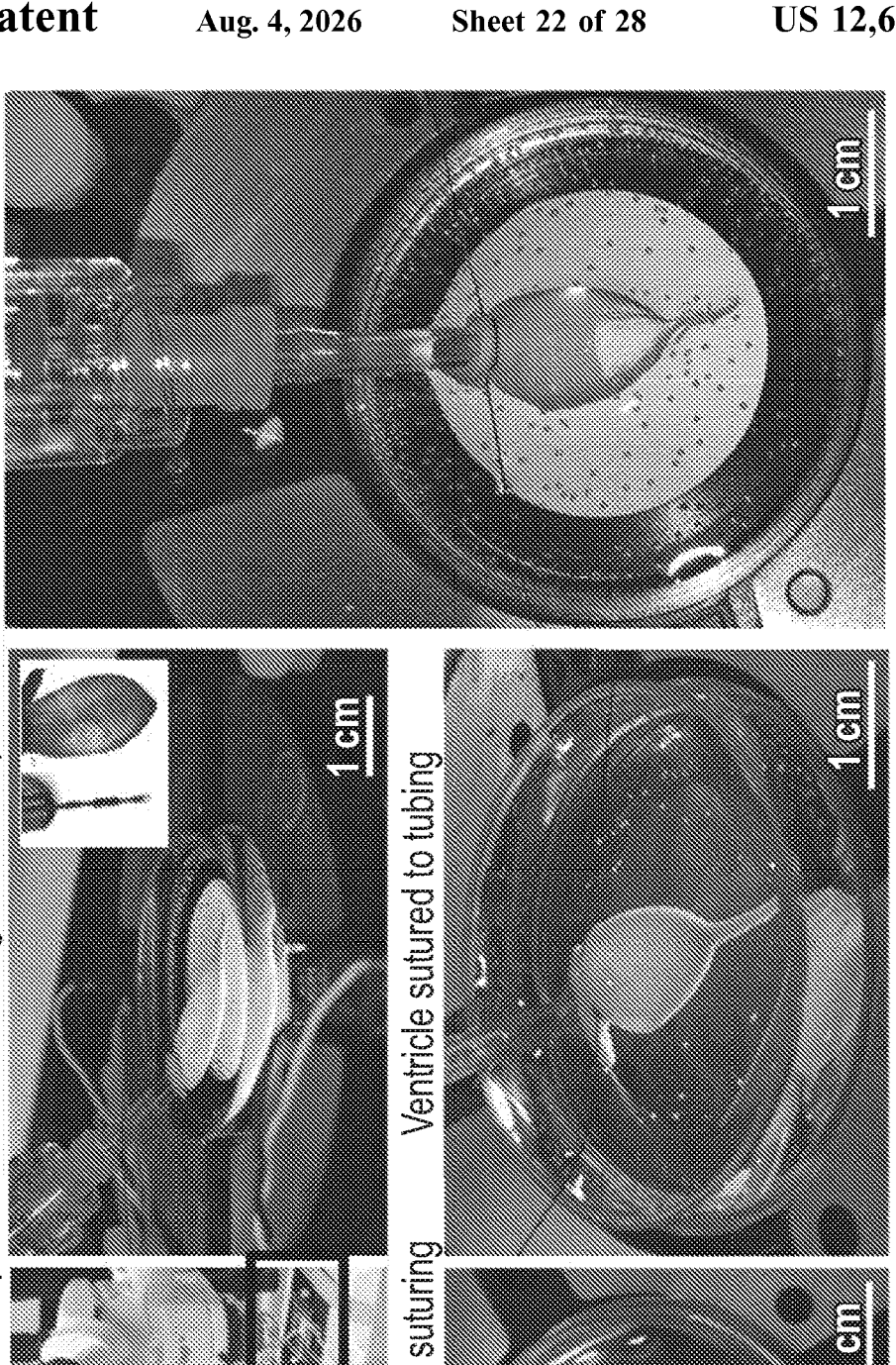

Intra-ventricular pressure and volume were measured simultaneously using a Millar MPVS-Ultra single segment foundation system for rats with SPR-869NR rat pressure-volume (PV) catheters (ADInstruments, Colorado Springs, CO). Catheter calibration and PV experiments were performed in freshly prepared Tyrode's solution. First, tissue-engineered ventricles were transferred to a 3.5 cm petri dish mounted on a temperature-controlled stage (Warner Instruments, Hamden Conn.) to maintain 35° C. working temperature. Ventricles were sutured to silicone tubing through which catheters were inserted (FIG. 12A). Data acquired at a sampling rate of 2,000 samples per second using manufacturer-supplied acquisition systems (Millar MPVS ultra, ADInstruments LabChart) and was exported for post-processing with custom Matlab scripts (MathWorks, Natick MA).

Figure 12C:
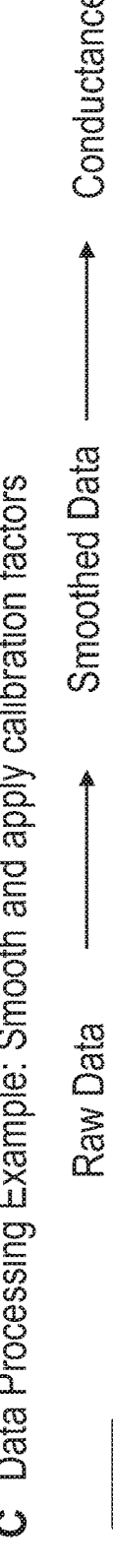
Figure 12C:
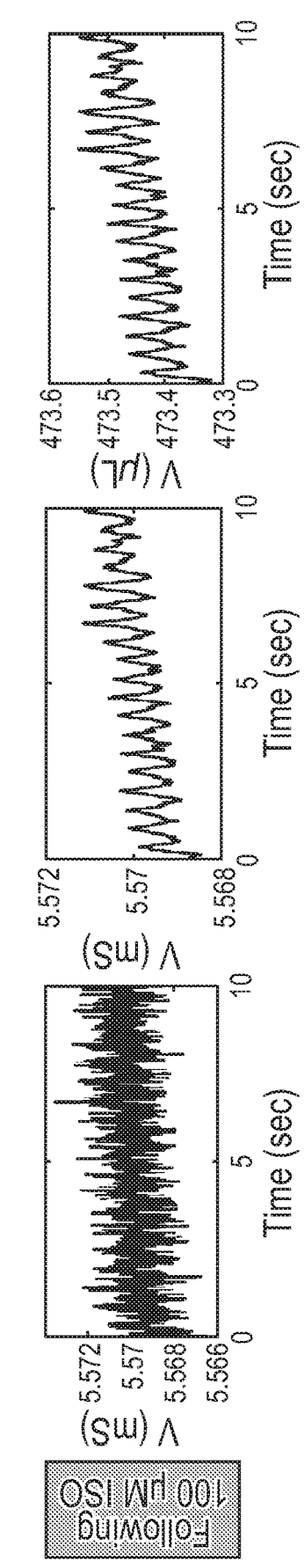

Catheter calibration. Catheters were equilibrated at 35° C. prior to use and calibrated for pressure using a manometer (Meriam M2; Meriam Process Technologies, Cleveland, OH) and volume using manufacturer-supplied cuvettes (Millar P/N 910-1048). A non-linear conductance/volume catheter response was observed (FIG. 12B. i). Separate scaffold-specific calibrations were performed, where cell-free scaffolds were inflated and deflated by manual application of pressure through a solution-filled syringe connected to the ventricle through a junction port. Here, the use of thin PCL-gelatin scaffold walls was validated in place of polycarbonate cuvettes or murine myocardium for which the system and catheters were designed and optimized (Pacher, P., et al. *Nat Protoc* 3, 1422-1434, 2008; Pearce, J. A., et al. *Conf Proc IEEE Eng Med Biol Soc* 2010, 3556-3558, 2010; Baan, J. et al. *Cardiovasc Res* 15, 328-334, 1981; Baan, J. et al. *Circulation* 70, 812-823, 1984; Raghavan, K. et al. *IEEE Trans Biomed Eng* 56, 2044-2053, 2009; and Clark, J. E. & Marber, M. S. *Exp Physiol* 98, 614-621, 2013). Volume estimated by calculating the slope of measured conductance versus cuvette volume (FIG. 12B i) or by scaffold filling (FIG. 12B ii) were in good agreement within a relevant working volume range of ~300-600 µL. In some cases, pressure or volume signal noise and drift were reduced by post-processing using Matlab's smooth and polyfit functions (FIG. 12C). Pressure and volume signals were normalized by polynomial background subtraction to reduce unwanted signal drift from large data sets, clarifying frequency-domain analysis of ventricle beat rates over these time periods (FIGS. 13A-13D).

β-adrenergic response of tissue-engineered ventricles. The contractile response of tissue-engineered ventricles to increasing concentrations of the β-adrenergic agonist isoproterenol was measured as follows. A 100 mM stock solution of isoproterenol (Sigma-Aldrich) containing 110 µM ascorbic acid (Sigma-Aldrich) and 45 µM EDTA (Sigma-Aldrich) was prepared in Tyrode's solution and stored at −20° C. Working concentrations were prepared fresh for each experiment by serial 10-fold dilution and kept on ice and protected from light during experiments. The engineered tissues were exposed to concentrations of isoproterenol ranging from $1 e^{-10}$ M to $1 e^{-4}$ M by cumulative addition of 1.0 log doses every 2 minutes. Pressure and volume recordings collected from the last 30 seconds of each measurement interval were converted to the frequency domain by Fast Fourier Transform (FFT) using Matlab and beat rates were estimated using Matlab's findpeaks function applied to pressure or volume FFT data (FIGS. 13A-13D).

Heart Bioreactor (HBR) Design and Fabrication

HBR designs were created using SolidWorks (DS Solid-Works Corporation, Waltham MA). HBR components were fabricated by rapid manufacturing providers (Proto labs, Maple Plain, MN) and by the staff of the John A. Paulson School of Engineering and Applied Sciences (SEAS) Scientific Instrument Shop at Harvard University. The HBR body consisted of three separated polycarbonate pieces that were assembled using stainless steel screws and silicone gaskets (FIGS. 1A-1E, 2A-2C, 3A-3D, 4A and 5A-5B). To increase optical transparency of HBR polycarbonate components, post-fabrication vapor-polishing was performed by methylene chloride vapor exposure in a chemical fume hood.

Echocardiography Echocardiographic images were acquired and videos of ventricle contraction using a Vevo 2100 system (VisualSonics, Toronto, Canada). A 21 MHz probe (~60 µm resolution, ~1.4 cm imaging depth) coupled to the HBR window through an index-matching gel was used.

Statistical Analysis

For analysis of tissue OOP and beat rate response to isoproterenol, one-way ANOVA between the compositional groups were conducted using SigmaPlot (v13.0, Systat Software Inc.). For pairwise comparison, the Tukey test was applied. For all statistical analyses, p-values less than 0.05 were considered statistically significant.

Results

Model Cardiac Chamber

To build a tissue-engineered ventricle chamber, a model cardiac chamber based on tabulated structural and functional properties of the human left ventricle was developed (Capulli et al., *Adv Drug Deliv Rev* 96, 83-102, 2016). The overall strategy to produce a scale-model of the human left ventricle chamber for pressure-volume catheterization is depicted in FIG. 6A, Specifically, the following criteria for the build were used (i) a scale-model of human left ventricle chamber would be built with the diastolic chamber volume of about 500 microliters (~2×rat, ~1/250 human); (ii) the ventricle wall would not be vascularized and its thickness limited to ~0.1 mm (~1/10 rat, ~1/100 human) to maintain high cell viability within the diffusion-limited environment; (iii) the ventricle scaffold material would be a well-known protein-polymer mixture to ensure production reproducibility using existing nanofiber platforms; (iv) ventricle tissues would be composed of a single cell type—the cardiomyocyte—to clarify effects of drug exposure tests that may otherwise be obfuscated by the presence of additional cell types; and (v) cardiomyocyte alignment would be circumferential throughout the scaffold, representing a thin walled approximation of the helical alignment within the native ventricular wall.

Ventricle Scaffold

Healthy ventricular musculature (myocardium) arises from precisely coordinated multiscale integration of physical forces transmitted between cells and the extra-cellular matrix (ECM), as well as between neighboring cells (Sheehy, S. P., Grosberg, A. & Parker, K. K. *Biomechanics and modeling in mechanobiology* 11, 1227-1239, 2012). The myocardial ECM is fibrillar, anisotropic, and provides nano-topographical cues that guide cardiomyocyte alignment and assembly (Kim, D. H. et al. *PNAS, USA* 107, 565-570, 2010), ultimately forming a helicoid structure that optimizes ejection fraction during ventricular contraction (Savadjiev, P. et al. *PNAS, USA* 109, 9248-9253, 2012). These features can be recapitulated using nanofibrous materials that are formed into cellular scaffolds with sufficient porosity to support cell infiltration and promote tissue morphogenesis (Capulli, A. K. et al., *Adv Drug Deliv Rev* 96, 83-102, 2016).

As depicted in FIGS. 6B-6C, and 7A-7B, a nanofiber ventricle chamber production strategy was developed based on pull-spinning fibers on a rotating ellipsoidal collector, which ensures roughly circumferential fiber alignment (Deravi, L. F. et al. *Macromolecular Materials and Engineering* 302, 2017). Polycaprolactone (PCL)/gelatin nanofibers were selected as the material of choice because they are biocompatible and biodegradable, they promote cell adhesion, provide sufficient structural integrity for ventricle culture and catheterization, and can be produced by a variety of nanofiber production platforms that include electrospinning and force-spinning methods (Capulli, A. K. et al., *Adv Drug Deliv Rev* 96, 83-102, 2016). Suitable devices and methods for fabrication of nanofibers and nanofiber scaffolds are also described in U.S. Pat. Nos. 9,410,267 and 9,738,046, and U.S. Patent Publication Nos. 2013/0312638 and 2015/0354094, the entire contents of each of which are incorporated herein by reference. PCL/gelatin nanofiber production by pull spinning and their use for skeletal muscle tissue engineering was previously described (Deravi, L. F. et al. *Macromolecular Materials and Engineering* 302, 2017). Currently disclosed is the use of scanning electron microscopy (SEM) to confirm that PCL/gelatin nanofiber scaffolds were structurally comparable with decellularized human left ventricle tissue (FIG. 10A).

Figures 10A, 10B:
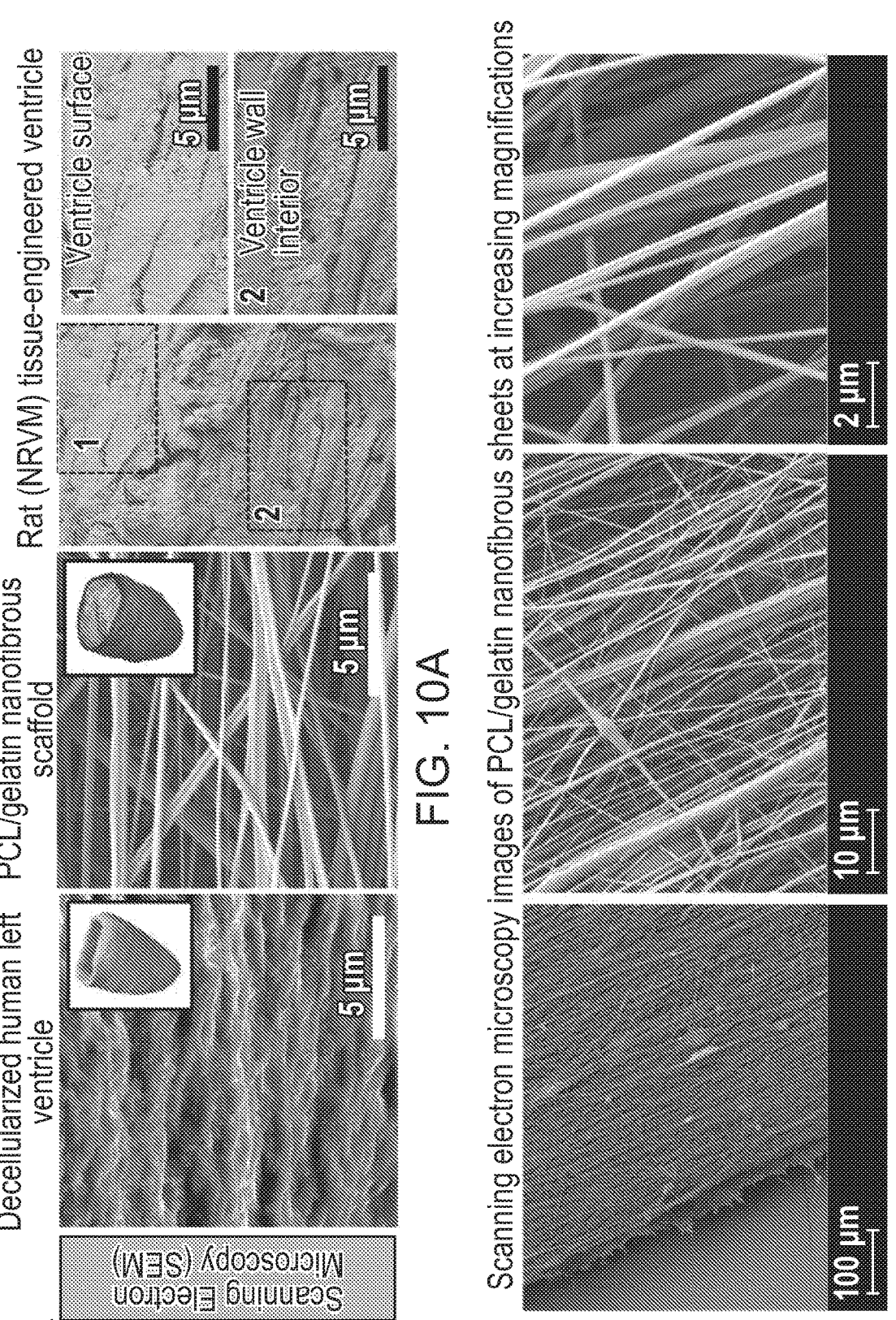
FIGS. 10A-10D illustrate polymer-protein nanofiber ultrastructure and biochemistry.
Figures 10C, 10D:
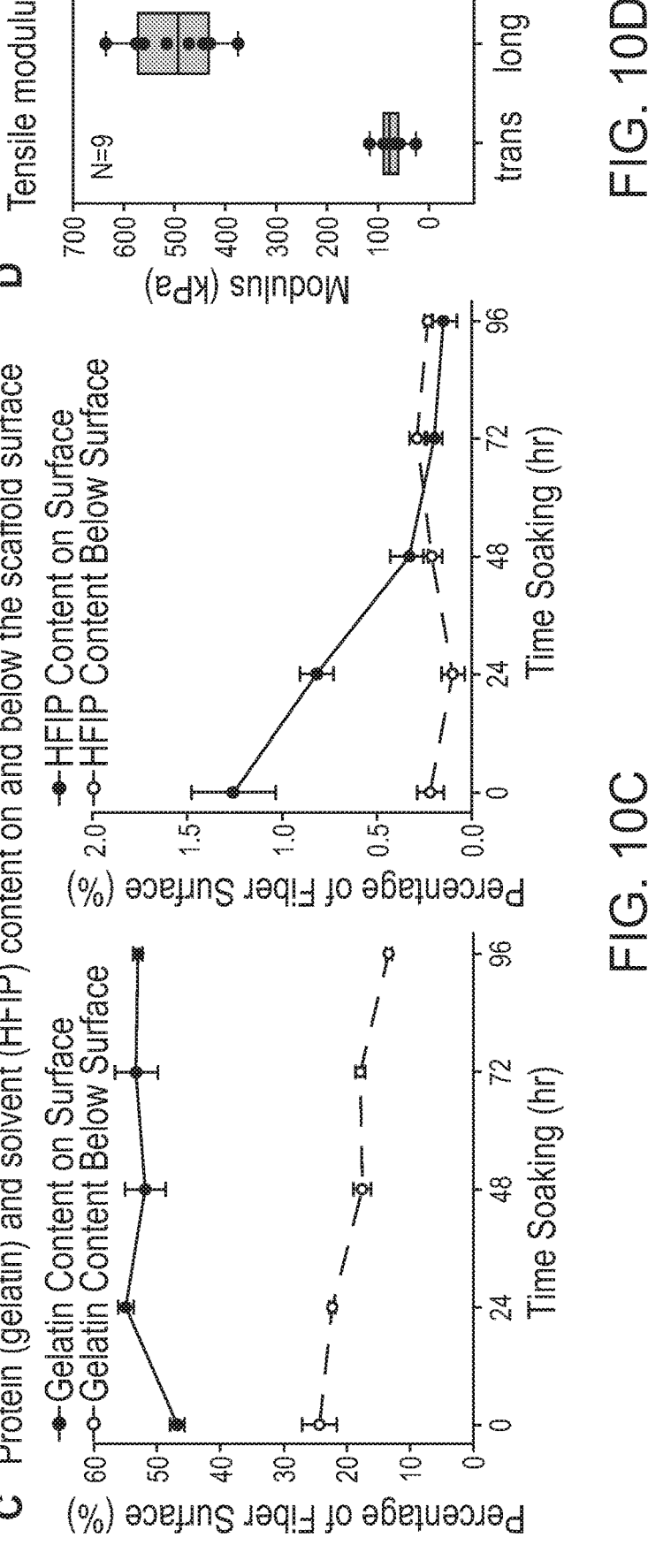

As depicted in FIG. 10B, gelatin incorporated into the nanofibers persisted for at least 4 days in aqueous solutions according to measurements made using X-ray photoelectron spectroscopy. As depicted in FIG. 10C, the tensile elastic modulus of the PCL/gelatin nanofiber scaffolds was anisotropic, with values measured longitudinally (in the direction parallel to the fiber axis), $E_L$=500±31 kPa, or transverse (in the direction perpendicular to the fiber axis), $E_T$=74±15 kPa. These properties demonstrate the fabrication of ventricle scaffolds that were both structurally stable and permissive to chamber contraction by cardiomyocyte shortening.

Given that natural contraction rates of cultured cardiomyocytes are ~60-120 bpm (~1-2 Hz) (Mannhardt, I. et al. *Stem Cell Reports* 7, 29-42, 2016; and Meiry, G. et al. *J Cardiovasc Electrophysiol* 12, 1269-1277, 2001), chamber scaffolds that were mechanically permissive to contraction in the same range were designed. To estimate the scaffold resonant bending frequency, $\omega_B$, a simple balance between the kinetic and potential energy of a thin fluid-loaded spherical elastic shell of modulus, E, radius, R, fluid density, $\rho_f$, and thickness, h was considered. The kinetic energy associated with the wall motion of amplitude, A, and frequency, $\omega_B$, scales as $$\rho_f R^3 A^2 \omega_B^2.$$

The potential energy of deforming the shell is dominated by long wavelength bending deformations and scales as $Eh^3 (A/R^2)^2 R^2$, where $Eh^3$ is the bending stiffness, and the curvature scales as $A/R^2$. Balancing the two yields $$Eh^3 (A^2 / R^2) \sim \rho_f R^3 A^2 \omega_B^2$$

so that $\omega_B \sim \overline{(Eh^3/\rho_f R^5)}$. Using parameter values from the PCL/gelatin nanofiber scaffolds (R=5 mm, h=0.1 mm, 50 kPa<E<500 kPa) gives bending resonant frequencies of 0.67 Hz<$f_B$<2 Hz, where $f_B$=$\omega_B/2\pi$, which match the contraction rates of cardiomyocytes. This demonstrates a natural design principal to engineer artificial ventricles as a function of the natural frequencies of cardiomyocyte contraction.

Tissue-Engineered Ventricle Chamber

Figure 6D:
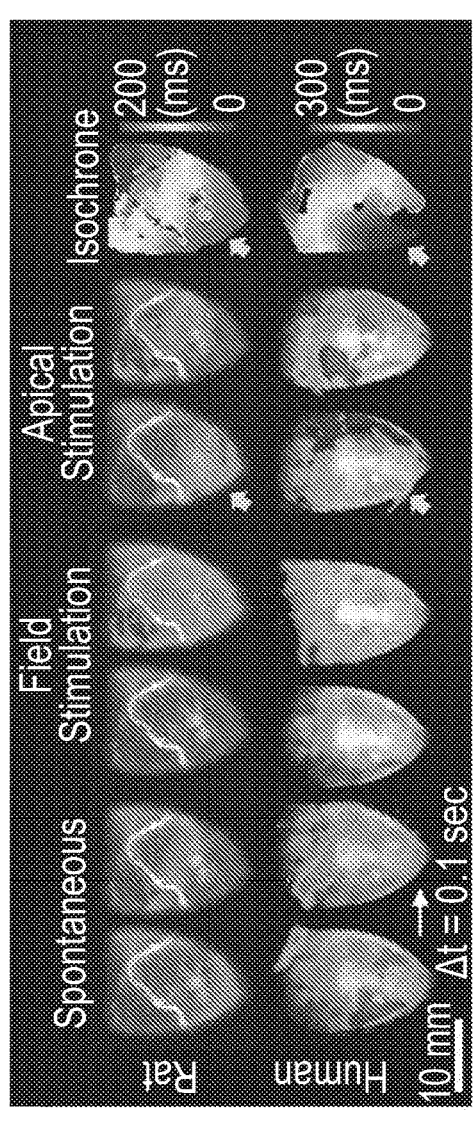
Figure 6C:
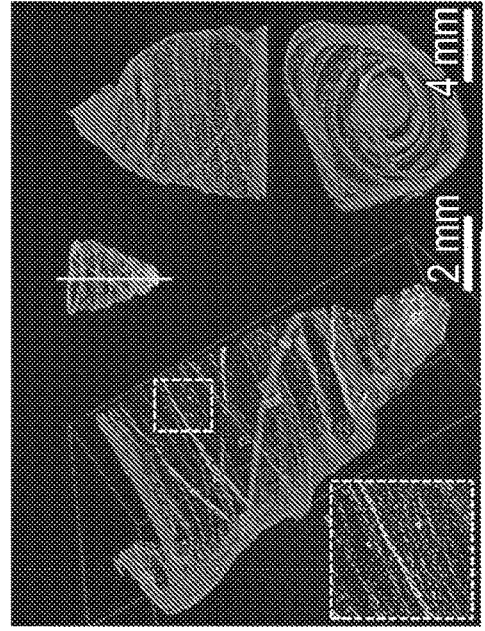
Figure 11C:
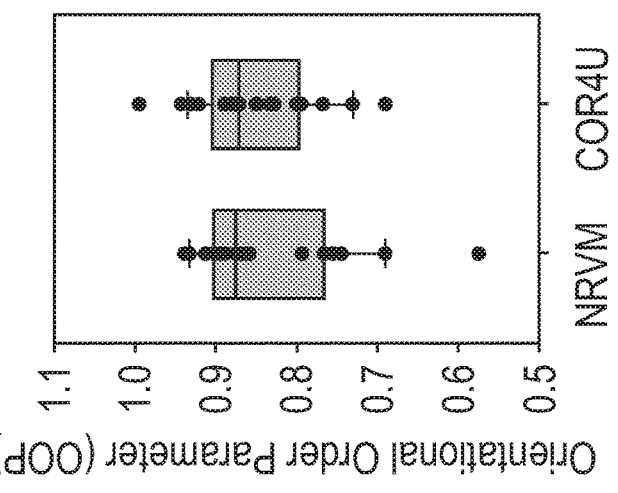
Figure 11C:
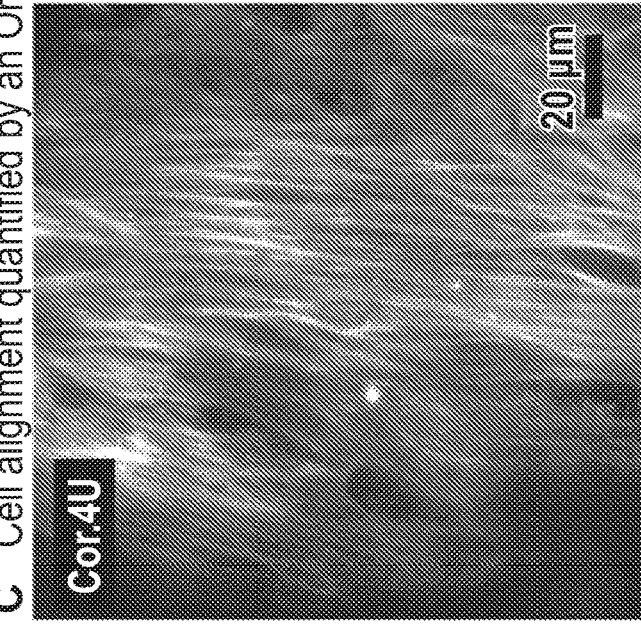

To build a tissue-engineered ventricle chamber, ventricle scaffolds were seeded with either neonatal rat ventricular myocytes (NRVM) or human induced pluripotent stem cell-derived cardiomyocytes (hiPSC-CM). Synchronous, coordinated ventricle contraction developed spontaneously after 3-5 days of culture and persisted for the duration of experimental procedures, conducted 14 days after seeding. Calcium imaging, which has been used as a surrogate for the action potential (Mandegar, M. A. et al. Cell stem cell, 2016.01.022, 2016), revealed continuous excitation propagation on the ventricle surfaces, confirming electrical continuity throughout the ventricle constructs (FIG. 6D). Mean calcium wavefront propagation velocity from apex to base was 9.33 cm/sec or 5.2 cm/sec for NRVM or hiPSC-CM ventricles, respectively. These values are comparable to those observed in tissues composed of immature cells where cell geometry, calcium handling, gap junction expression and spatial distribution, as well as other factors limit the conduction velocity when compared to mature tissues (Rohr, S. et al., *Circ Res* 83, 781-794, 1998; and Yang, X. L. et al., *Circulation research* 114, 511-523, 2014). As depicted in FIGS. 8A-8C and 11A-11C, immunostaining confirmed fiber-directed anisotropic cell alignment and infiltration within the chamber wall, enabling quantification of cell alignment using a metric known as the orientational order parameter (OOP) that ranges from zero (random organization) to one (perfect alignment) (Feinberg, A. W. et al. *Biomaterials* 33, 5732-5741, 2012; and Pasqualini, F. S. et al., *Stem Cell Reports* 4, 340-347, 2015). As depicted in FIG. 11C, both NRVM and hiPSC-CM ventricles showed high alignment based on OOP analysis of F-actin stains, with OOP values of 0.84±0.02 (NRVM) and 0.85±0.02 (hiPSC-CM).

Intra-Ventricular Pressure and Volume Measurements

Figures 9A, 9B:
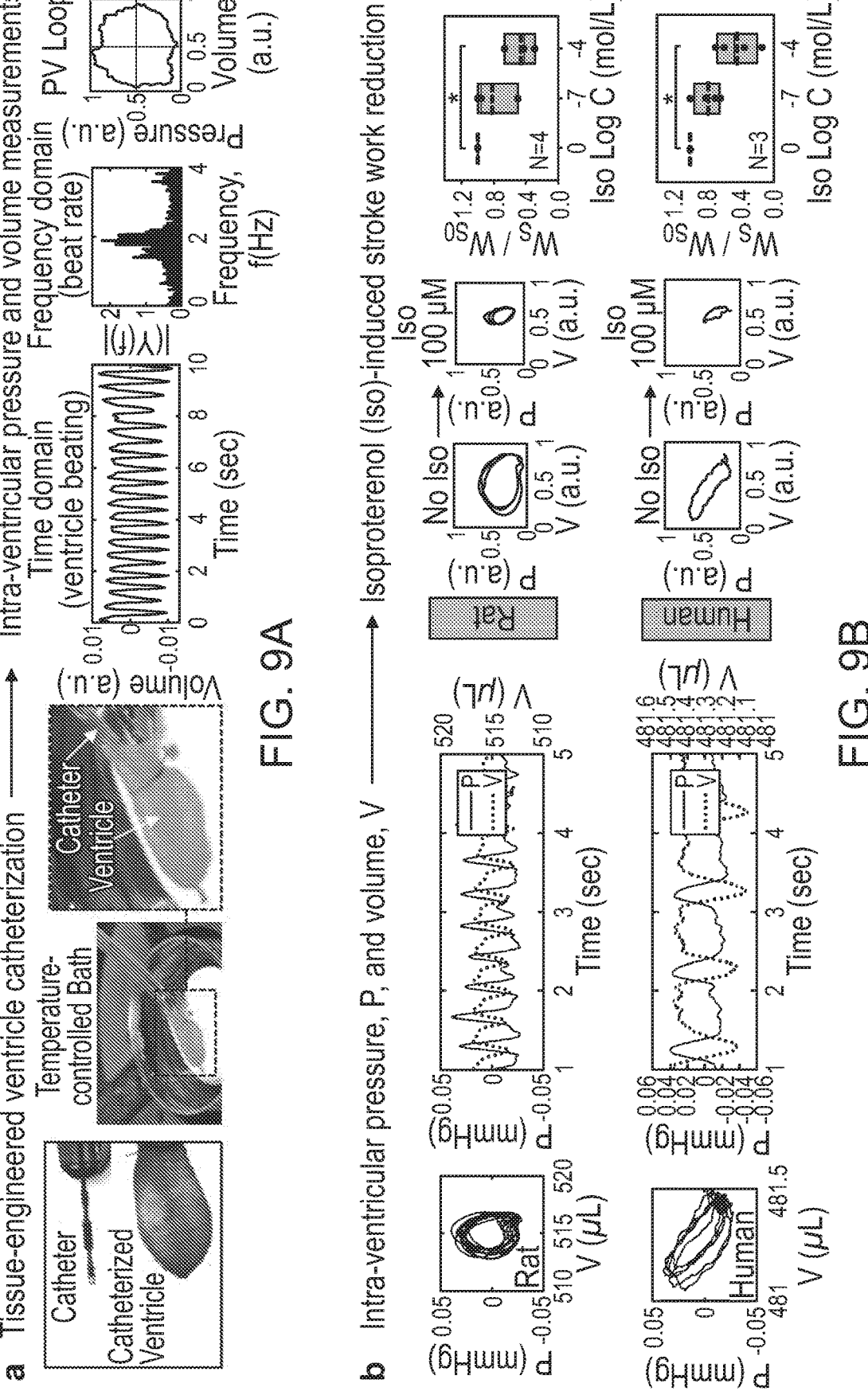
FIGS. 9A-9C illustrate intra-ventricular pressure-volume (PV) data obtained by tissue-engineered ventricle catheterization.
Figure 13A:
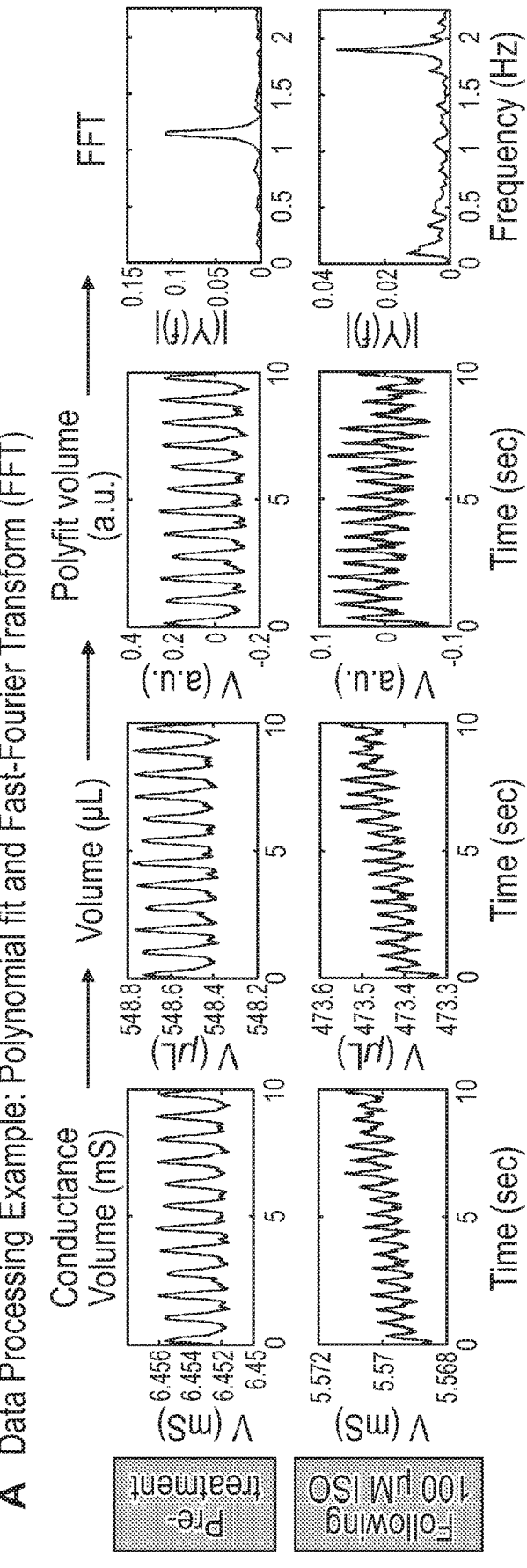
FIGS. 13A-13D illustrate time and frequency domain analysis of example tissue-engineered ventricle beat rates.
Figure 13B:
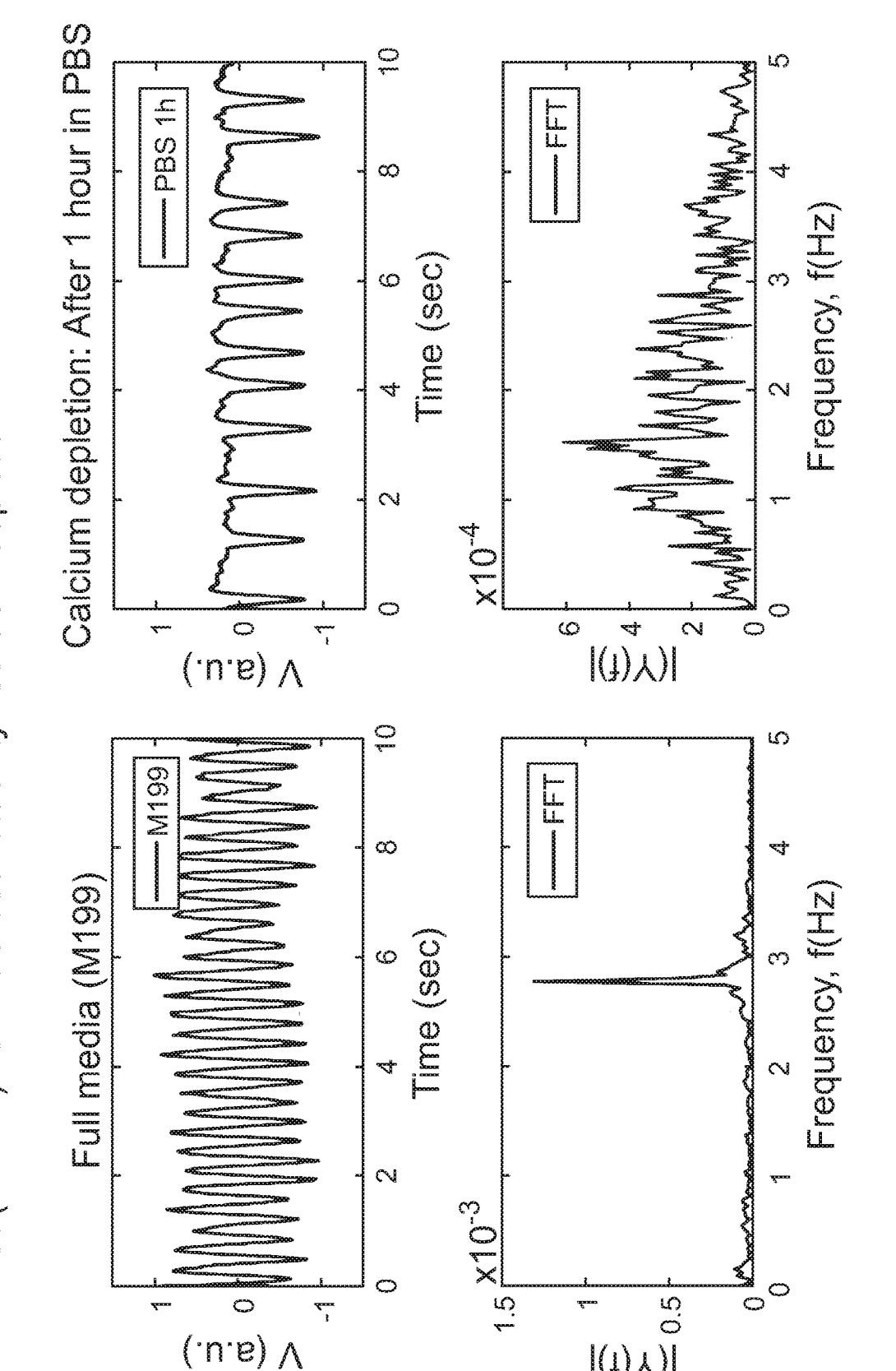
Figure 13C:
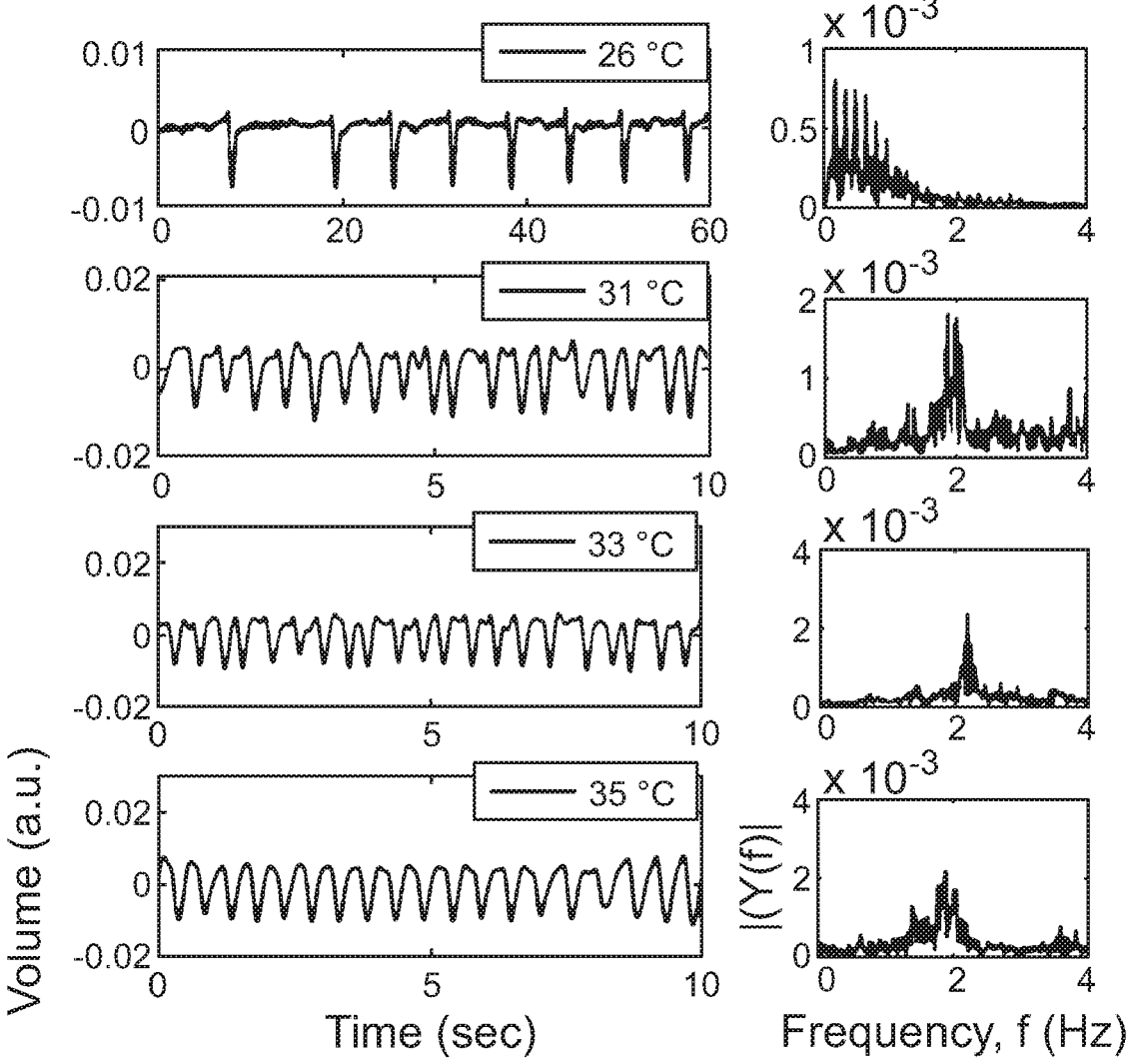

To determine whether the engineered ventricles exhibited in vivo-like chamber contraction, time-dependent intra-ventricular pressure and volume by catheterization were measured (FIGS. 9A-9C and 12A-12C), an established method for heart chamber performance evaluation (Burkhoff, D., et al. *American journal of physiology. Heart and circulatory physiology* 289, 2005). Pressure/volume (PV) catheters were inserted into the tissue-engineered ventricles from base to apex through tubing over which the ventricle base was sutured (FIG. 12A). Catheter calibrations (FIG. 12B) and acquired data at 2,000 samples per second for export and analysis (FIG. 12C) were performed. Exported data was processed for time and frequency-domain analysis, which are commonly used to quantitatively assess cardiovascular function (Akselrod, S. et al. *Science* 213, 220-222, 1981; and Fenske, S. et al. *Nat Protoc* 11, 61-86, 2016) (FIGS. 13A-13D). As an initial validation of the experimental platform, ventricle contractile responses to gross alterations in the composition of the extracellular bath solution were investigated. Whereas regular beat frequencies were observed in calcium-containing M199 or Tyrode's solution, exposure to calcium-free PBS led to broad beat rate distributions (FIG. 13B). Exposure to bath temperatures less than ~30° C. showed an expected reduction in beat rate as judged by a shift in the frequency spectrum as bath temperature was decreased from physiological 37° C. (FIG. 13C). These results demonstrate that tissue-engineered ventricles can be functionally interrogated and myocardial performance assessed using catheter-based pressure-volume measuring platforms. To visualize the relationship between pressure and volume change during cardiac contraction cycles, PV loops for both rat (NRVM) and human (hiPSC-CM) ventricles from PV catheter measurements were plotted. As depicted in FIG. 9B, measured differences in chamber pressure were ~50 μmHg (rat or human) and the volume change was ~5 μL (rat) or 1 μL (human). Thus, ejection fractions were ~1% (rat) or ~0.2% (human) and stroke work was $W_S$~0.25 mmHg×μL (rat) or $W_S$~0.05 mmHg×μL (human).

Figure 9C:
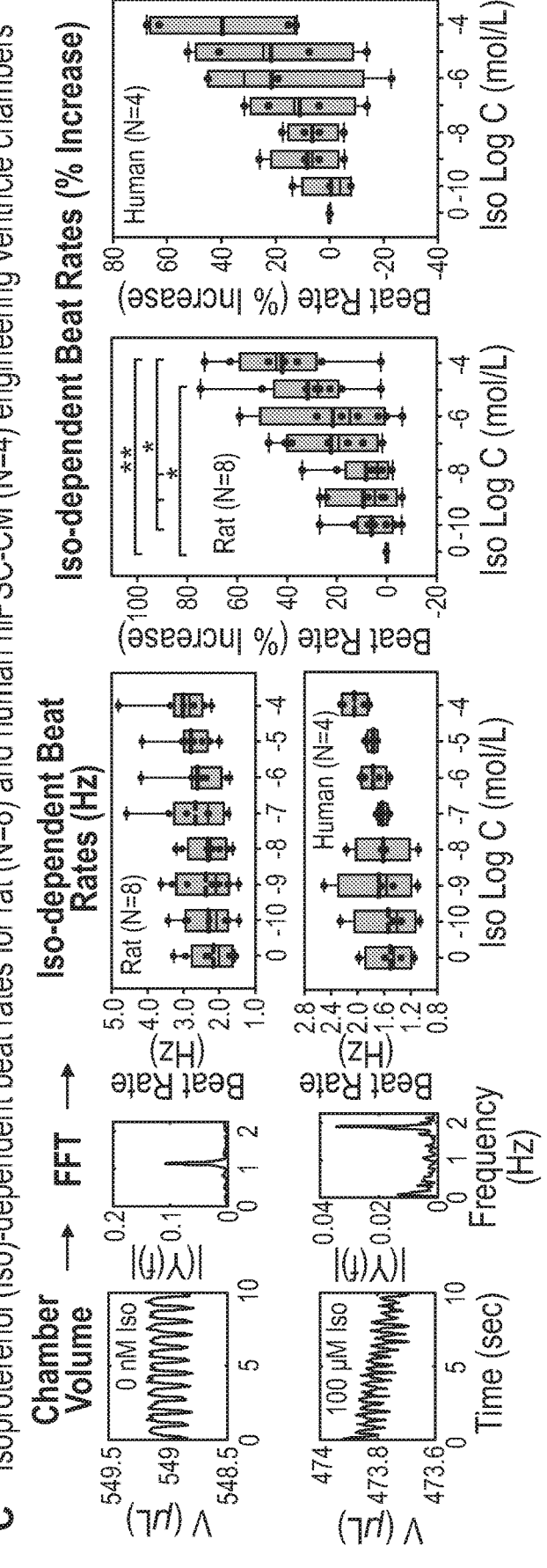
Figure 13D:
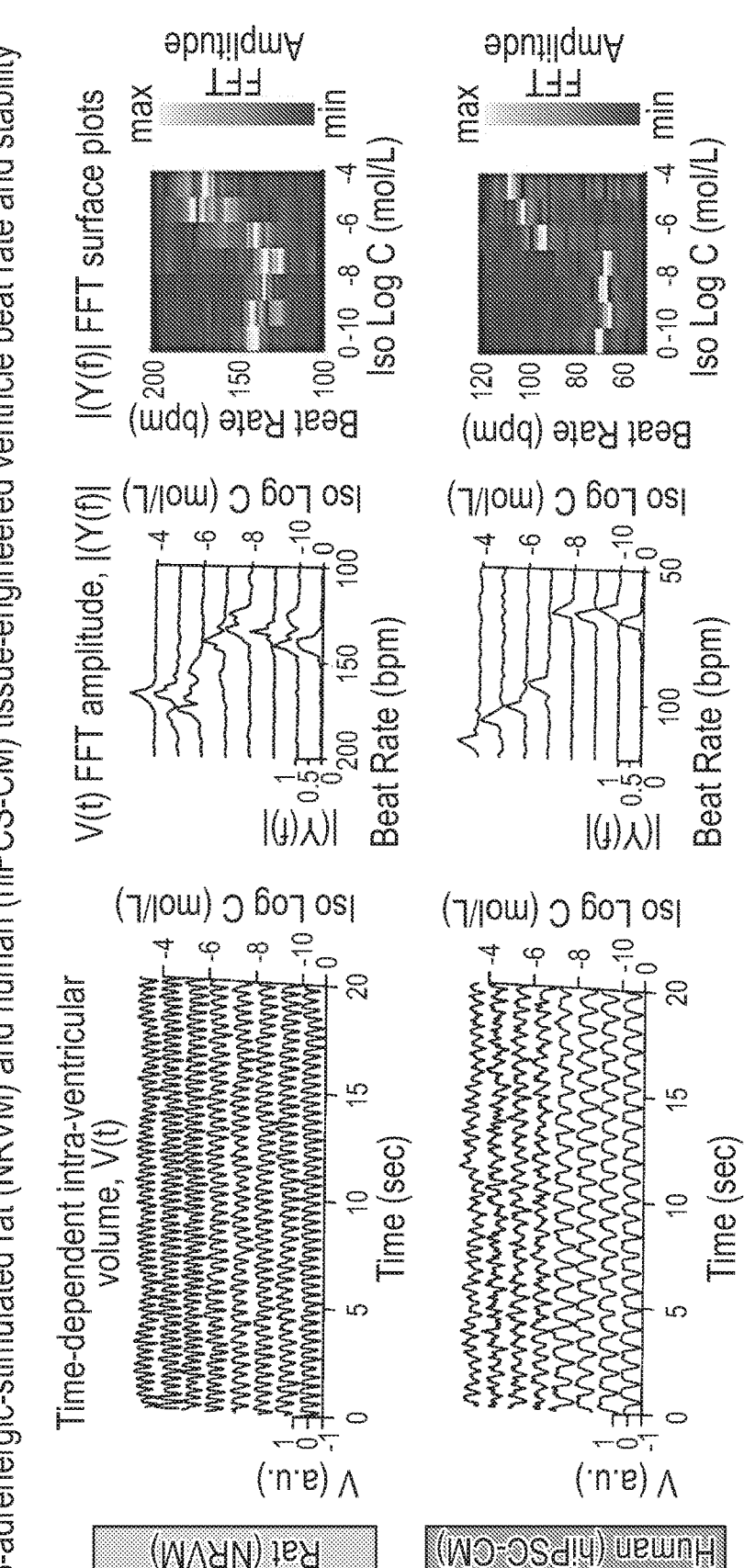

A fundamental aspect of myocardial function is the response to adrenergic agonists, which has been studied extensively in both rodents and humans, making β-adrenergic response a good test of the ability of our engineered ventricles to recapitulate normal cardiac physiological drug responses (Barrett, A. M. & Carter, *J. Br J Pharmacol* 40, 373-381, 1970; and Brito-Martins, et al. *Br J Pharmacol* 153, 751-759, 2008). To assess the chronotropic response of the engineered ventricles to a β-adrenergic receptor agonist, the engineered ventricles were subjected to concentrations of isoproterenol ranging from 1 $e^{-10}$ M to 1 $e^{-4}$ M. As depicted in FIGS. 9B and 9C, pressure/volume loops measured before and after isoproterenol exposure showed an isoproterenol-induced reduction in stroke work, concomitant with an increase in beat frequency. Continuous intraventricular pressure and volume measurements enabled frequency-domain analysis of the chronotropic response of either NRVM or hiPSC-CM ventricles (FIG. 13D). As depicted in FIG. 9C, ventricle beat rates showed a positive chronotropic response over the concentration range in both the NRVM and hiPSC-CM ventricles, for healthy NRVM, hiPSC-CM, engineered hiPSC-CM cardiac tissues, and human patients (Simpson, P. & Savion, S. *Circ Res* 50, 101-116, 1982; Moretti, A. et al. *N Engl J Med* 363, 1397-1409, 2010; Mannhardt, I. et al. "Human engineered heart tissue: Analysis of contractile force." *Stem Cell Reports* 7, 29-42, 2016; and Koglin, J. et al., *J Am Coll Cardiol* 23, 678-683, 1994). The spontaneous beat rate of NRVM ventricles (~130±15 bpm) was higher than hiPSC-CM ventricles (~85±15 bpm), and both increased by ~40% following exposure to $10^{-4}$ M isoproterenol.

Bioreactor for Modular Assembly of Ventricles and Valves

Figure 4A:
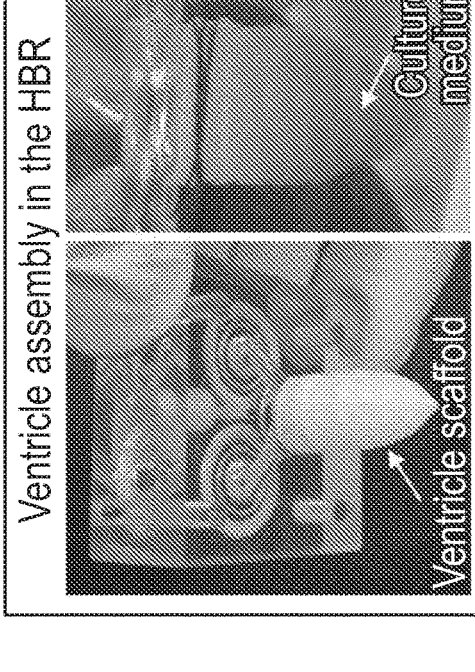
FIGS. 4A-4C depict a system that can be used as a HBR for tissue-engineered ventricle culture, assisted contraction, and instrumentation in accordance with some embodiments.
Figure 4A:
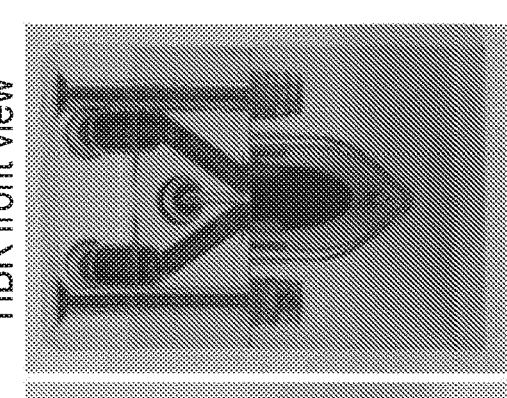
Figure 4A:
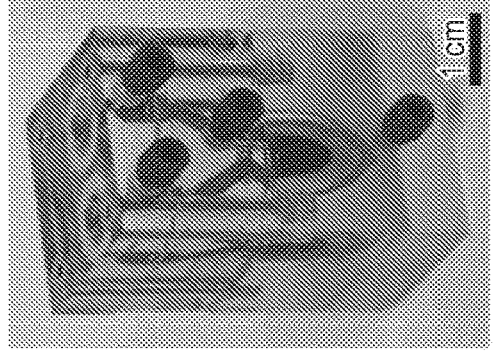
Figure 4A:
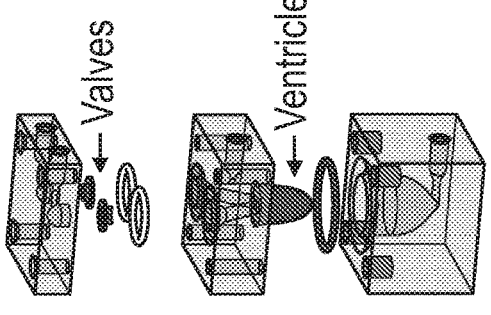
Figure 4B:
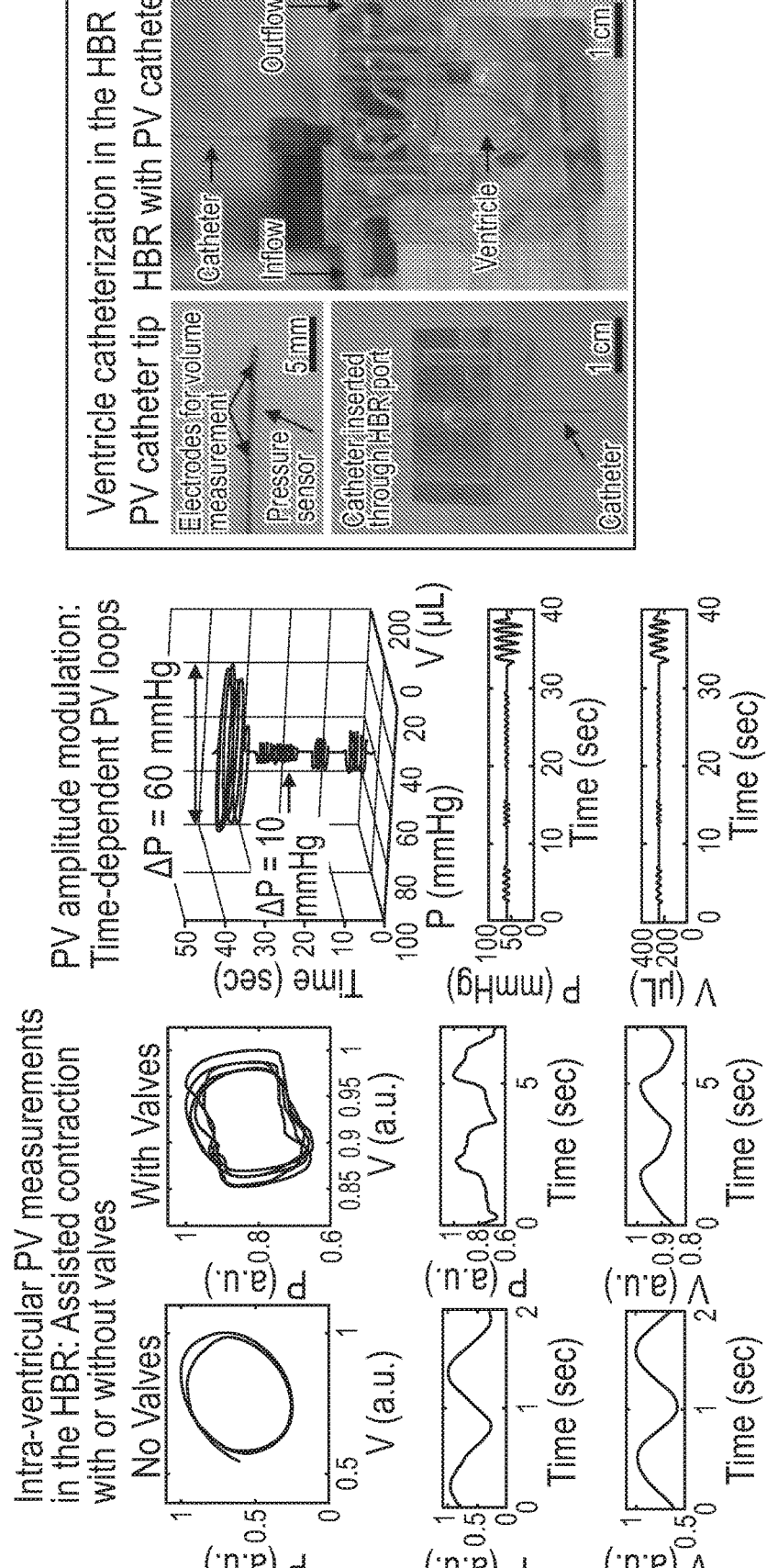
Figure 4C:
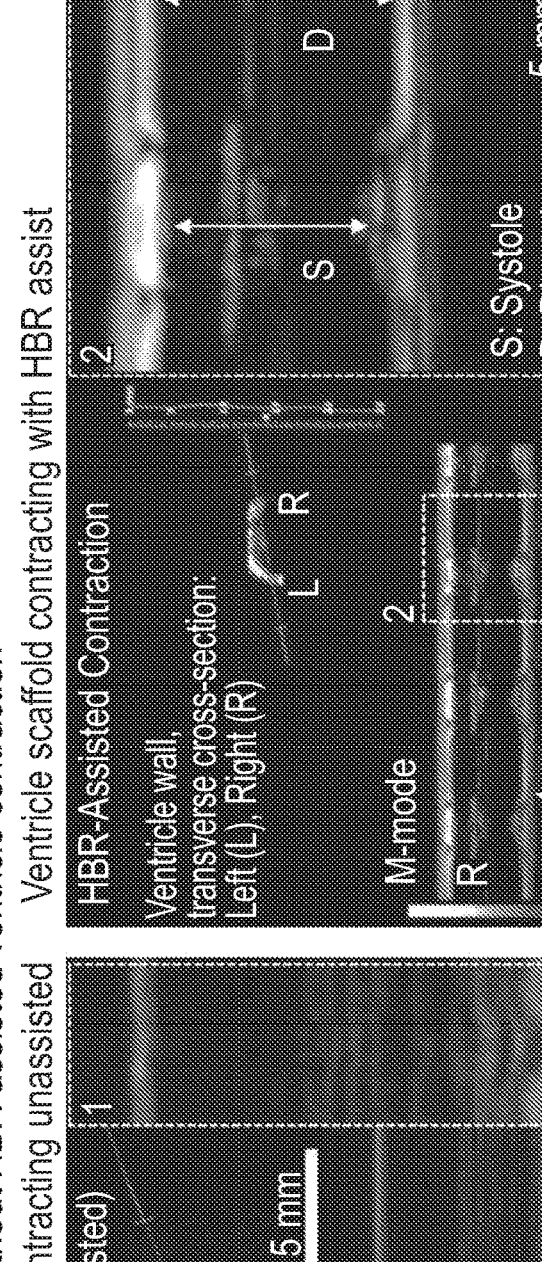
Figure 5A:
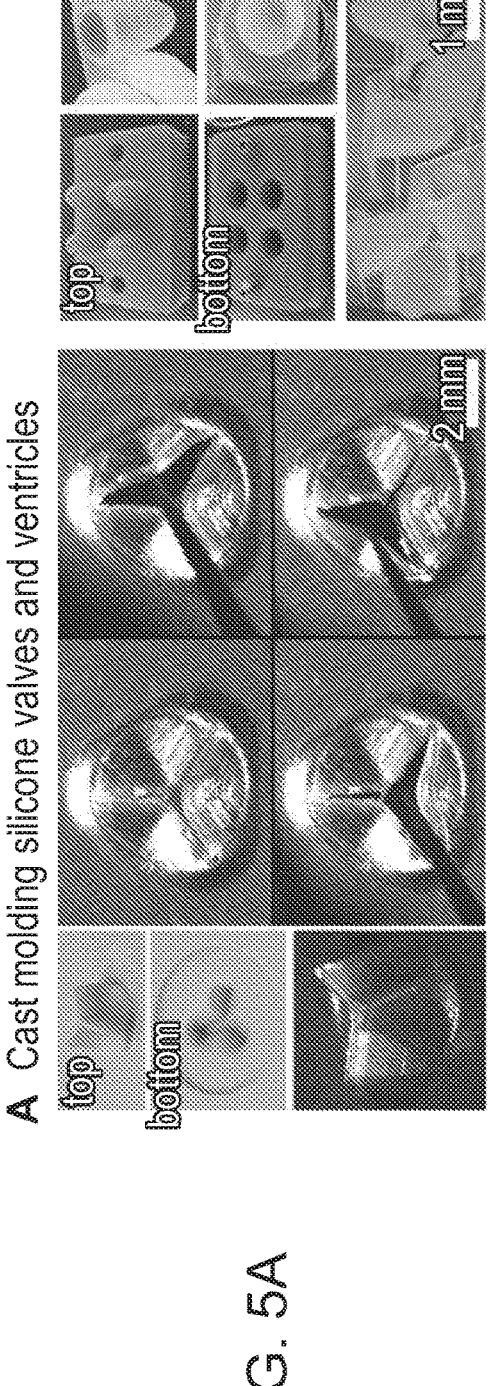
FIG. 5A includes images of cast-molding of silicone tricuspid valves and ventricle chambers in accordance with some embodiments. The cast-molding procedure produces optional valve or ventricle components that can be assembled within a system, such as an HBR, to support tissue-engineered ventricle assisted contraction and fluid pumping.
Figure 5B:
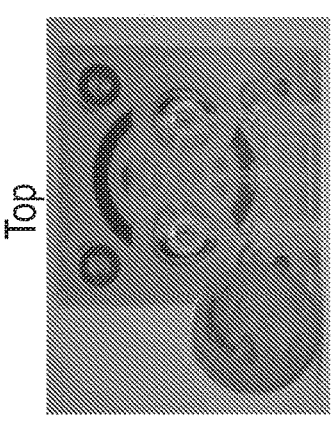
FIG. 5B includes images of various example HBR systems produced according to some embodiments of the present disclosure.
Figure 5B:
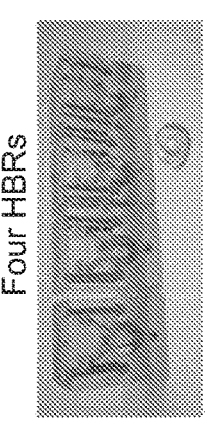
Figure 5B:
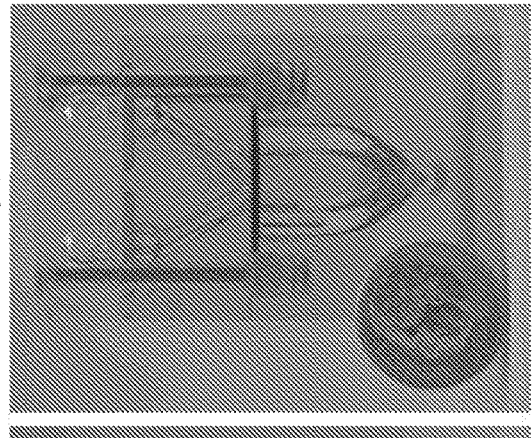
Figure 5B:
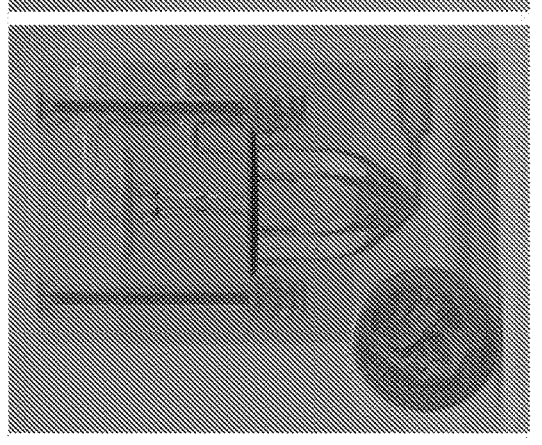
Figure 5B:
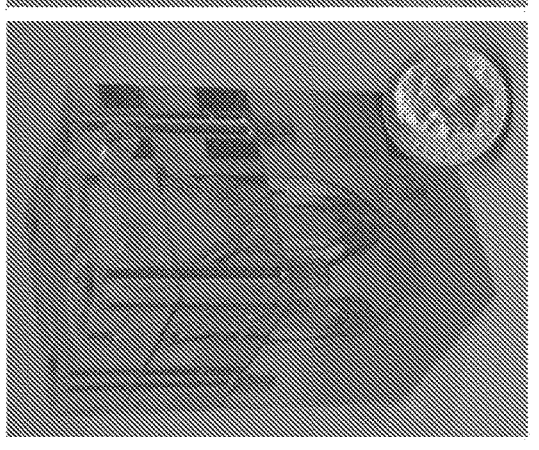

Laboratory models of biological tissues often benefit from culture in bioreactors or microfluidic platforms where fluid exchange can be automated and in situ measurements obtained. To support tissue-engineered ventricle culture, a self-contained instrumented heart bioreactor (HBR) was built (FIGS. 1A-1E, 2A-2C, 3A-3D, 4A-4C and 5A-5B). As depicted in FIGS. 1A-1E and 4A, the HBR includes both intra- and extra-ventricular flow loops, separate chambers for optional valve inserts, and additional access ports for catheters, electrocardiographic (ECG) recording electrodes, electrical pacing electrodes, or optical pacing fiber optics. Cyclic pressure applied to the extra-ventricular loop drives intra-ventricular fluid flow via assisted ventricle contraction, and unidirectional flow can be achieved using commercially available valves or with custom valve inserts in the HBR. Figs. FIGS. 2A-2C, 3A-3D, 4A and 5A-5B depict assisted pumping in the absence of drugs by controlling pressure delivered to the external (assist) channel using a pressure-driven programmable pump (OB1; Elvesys, Paris, France) and cast-molded silicone tricuspid valves to direct flow. As depicted in FIG. 4B, in this configuration, cultured ventricles can be exposed to externally-controlled physiological or pathological pressure variations and PV loops acquired with or without valves, emphasizing the potential to study heart failure where differential effects of various organ sub-structures are measured. Lastly, to highlight the translational nature of this platform, ventricle contraction by ultrasound through removable elastomeric windows in the HBR was monitored (FIG. 4C). Using small animal echocardiography equipment, both unassisted natural spontaneous ventricle contraction (FIG. 4C, left) and HBR-assisted contraction (FIG. 4C, right) were recorded. Echocardiography performed in the absence of extra-ventricular tissues can improve image clarity compared with in vivo studies, underscoring the advantage of organ modularity in our HBR.

These results demonstrate the feasibility of extending in vitro human heart models to include functional 3D cardiac chambers.

The myocardium is a composite in which the dominant stiffness shifts from myocytes to the ECM with increasing strain (Chaturvedi, R. R. et al. "Passive stiffness of myocardium from congenital heart disease and implications for diastole." *Circulation* 121, 979-988, 2010), emphasizing the ECM's role maintaining structural integrity. The engineered scaffold disclosed herein provide sufficient structural integrity for ventricle culture and they guided cardiomyocyte assembly The spontaneous beat rates of the engineered ventricles were similar to other in vitro assays based on NRVM or hiPSC-CM and they responded appropriately to isoproterenol (Meiry, G. et al. *J Cardiovasc Electrophysiol* 12, 1269-1277, 2001; Mannhardt, I. et al. *Stem Cell Reports* 7, 29-42, 2016; Eder, A., Vollert, I., Hansen, *A. & Eschenhagen, T. Adv Drug Deliver Rev* 96, 214-224, 2016; and Mathur, A. et al. *Sci Rep* 5, 8883, 2015), showing moderate positive chronotropy (~40% beat rate increase).

In summary, the foregoing example demonstrates the use of tissue-engineered ventricles for in vitro cardiology using intra-ventricular pressure and volume measurements. 3D nanofibrous scaffolds seeded with either primary rat cardiomyocytes or human stem cell-derived cardiomyocytes supported tissue morphogenesis, enabling organ-level measurement of ventricle function. Tissues based on primary rat cardiomyocytes and human stem cell-derived cardiomyocytes were evaluated because rat is the industry standard for the study of heart disease in vitro and in vivo, yet the use of human models is highly sought. Taken together, the data presented herein demonstrate the fabrication of tissue-engineered ventricles, and a modular bioreactor platform suitable for in situ instrumentation and functional assessment, thereby providing a platform for in vitro cardiology studies that increasingly translate to clinical outcomes.

Approximating language, as used herein throughout the specification and claims, may be applied to modify any quantitative or qualitative representation that could permissibly vary without resulting in a change in the basic function to which it is related. Accordingly, a value modified by a term such as "about" or numerical ranges is not to be limited to a specified precise value, and may include values that differ from the specified value. In at least some instances, the approximating language may correspond to the precision of an instrument for measuring the value.

While the disclosure has been described in detail in connection with only a limited number of aspects and embodiments, it should be understood that the disclosure is not limited to such aspects. Rather, the disclosure can be modified to incorporate any number of variations, alterations, substitutions, or equivalent arrangements not heretofore described, but which are commensurate with the scope of the claims. Additionally, while various embodiments of the disclosure have been described, it is to be understood that aspects of the disclosure may include only some of the described embodiments. Accordingly, the disclosure is not to be seen as limited by the foregoing description, but is only limited by the scope of the appended claims.

We claim:
1. A system, comprising:
a housing comprising:
   a cavity housing component defining a cavity extending from an opening in a first surface of the cavity housing component; and a support housing component having a sealing surface configured to sealingly engage the first surface of the cavity housing component thereby sealing the opening and defining a fluid chamber having a sealing end defined by the support housing component, the support housing component defining a pair of intra-hollow tissue structure flow channels connected to the sealing end of the fluid chamber, the support housing component including a support ring configured to engage and support an open end of a hollow tissue structure at the sealing end of the fluid chamber with the hollow tissue structure suspended in the fluid chamber and supported only at the support ring, the hollow tissue structure having only one open end, and the support housing component configured to fluidly couple the pair of intra-hollow tissue structure flow channels with each other and with an interior of the hollow tissue structure via an intra-hollow tissue structure flow path at the sealing end of the fluid chamber;

the housing defining a pair of extra-hollow tissue structure flow channels fluidly coupled to the fluid chamber, at least one of the pair of extra-hollow tissue structure flow channels defined by the cavity housing component, and the housing configured to receive the hollow tissue structure within the fluid chamber with the hollow tissue structure engaged and supported by the support ring at the sealing end of the fluid chamber to fluidly couple the pair of extra-hollow tissue structure flow channels via an extra-hollow tissue structure flow path extending between an exterior of the hollow tissue structure and a surface of the fluid chamber at least partially surrounding the hollow tissue structure.

2. The system of claim 1, further comprising the hollow tissue structure disposed in the fluid chamber and fluidly coupling the pair of intra-hollow tissue structure flow channels together.

3. The system of claim 2, wherein the hollow tissue structure comprises a population of cells.

4. The system of claim 3, wherein the hollow tissue structure comprising the population of cells is a natural hollow tissue structure or an engineered hollow tissue structure.

5. The system of claim 4, wherein the natural hollow tissue structure or the engineered hollow tissue structure is a ventricle, a heart, a stomach, an intestine, a uterus, or a bladder.

6. The system of claim 2, wherein the hollow tissue structure is at least partially coated with a sealant.

7. The system of claim 2, wherein the hollow tissue structure is fabricated by:

forming micron, submicron or nanometer dimension polymeric fibers, the polymeric fibers configured in a shape of the hollow tissue structure; and seeding cells onto the polymeric fibers.

8. The system of claim 2, wherein the housing and hollow tissue structure form a bioreactor.

9. The system of claim 1, further comprising at least one valve associated with at least one of the pair of intra-hollow tissue structure flow channels for controlling fluid flow through at least one of the intra-hollow tissue structure flow path and the extra-hollow tissue structure flow path.

10. The system of claim 1, further comprising a first fluid source fluidly coupled to the pair of intra-hollow tissue structure flow channels for supplying a first fluid and a second fluid source fluidly coupled to the pair of extra-hollow tissue structure flow channels for supplying a second fluid.

11. The system of claim 1, further comprising a sensor at least partly disposed in the intra-hollow tissue structure flow path or fluidly coupled with the intra-hollow tissue structure flow path.

12. The system of claim 1, wherein the pair of intra-hollow tissue structure flow channels converge at the support ring.

13. The system of claim 1, wherein the hollow tissue structure is a ventricular hollow tissue structure.

14. The system of claim 1, wherein the support housing component includes:

a middle housing component having a mating surface, the sealing surface of the support housing component being a surface of the middle housing component opposite the mating surface, the middle housing component defining a first section of each of the pair of intra-hollow tissue structure flow channels; and an outer housing component having a complementary mating surface to the mating surface of the middle housing component, the outer housing component defining a second section of each of the pair of intra-hollow tissue structure flow channels;

for each of the pair of intra-hollow tissue structure flow channels, the mating surface of the middle housing component and the complementary mating surface of the outer housing component each configured to hold a valve between the first section of the intra-hollow tissue structure flow channel and the second section of the intra-hollow tissue structure flow channel.

15. The system of claim 1, wherein an outer wall of the hollow tissue structure separates the intra-hollow tissue structure flow path and the extra-hollow tissue structure flow path in the fluid chamber.

16. The system of claim 1, where in the system is configured such that a change in a fluid pressure differential between a first fluid in the intra-hollow tissue structure flow path and a second fluid in the extra-hollow tissue structure flow path deflects at least a portion of the hollow tissue structure causing a change in flow of the first fluid through the pair of intra-hollow tissue structure flow channels.

17. A method of forming the system according to claim 1, the method comprising: attaching the hollow tissue structure to the support ring of the support housing component of the system;

sealingly engaging the support housing component with the cavity housing component thereby fluidly coupling the pair of intra-hollow tissue structure flow channels via the intra-hollow tissue structure flow path into the fluid chamber, through an interior of the hollow tissue structure, and out of the fluid chamber, and fluidly coupling the pair of extra-hollow tissue structure flow channels via the extra-hollow tissue structure flow path extending between an exterior of the hollow tissue structure and a surface of the fluid chamber.

18. A method for identifying a compound that modulates a hollow tissue function, comprising:

providing the system of claim 1;

contacting the hollow tissue structure with a test compound; and determining the effect of the test compound on the hollow tissue function in the presence and absence of the test compound, wherein a modulation of the hollow tissue function in the presence of the test compound as compared to the hollow tissue function in the absence of the test compound indicates that the test compound modulates the hollow tissue function, thereby identifying the compound that modulates a hollow tissue function.

19. A method for identifying a compound useful for treating or preventing a hollow tissue disease, comprising:

providing the system of claim 1;

contacting the hollow tissue structure with a test compound; and determining the effect of the test compound on a hollow tissue function in the presence and absence of the test compound, wherein a modulation of the hollow tissue function in the presence of the test compound as compared to the hollow tissue function in the absence of the test compound indicates that the test compound modulates the hollow tissue function, thereby identifying a compound useful for treating or preventing the hollow tissue disease.

* * * * *